United States Patent
Grovender et al.

(10) Patent No.: US 8,512,282 B2
(45) Date of Patent: *Aug. 20, 2013

(54) CATHETER WITH SKIVED TUBULAR MEMBER

(75) Inventors: Adam D. Grovender, Brooklyn Park, MN (US); Benjamin Grundale, Plymouth, MN (US); Thomas Knowles, Hermantown, MN (US); Roger W. McGowan, Otsego, MN (US); Todd Rowe, Excelsior, MN (US); Charles Rundquist, White Bear Lake, MN (US); Chuanjing Xu, Chaska, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/295,473

(22) Filed: Nov. 14, 2011

(65) Prior Publication Data

US 2012/0059336 A1  Mar. 8, 2012

Related U.S. Application Data

(63) Continuation of application No. 12/389,393, filed on Feb. 20, 2009, now Pat. No. 8,057,430.

(51) Int. Cl.
*A61M 31/00* (2006.01)

(52) U.S. Cl.
USPC .................. 604/103.04; 604/96.01; 604/523; 604/524; 604/525

(58) Field of Classification Search
USPC .......................... 604/96.01, 103.04, 523–525
See application file for complete search history.

(56) References Cited

U.S. PATENT DOCUMENTS

| 4,762,129 A | 8/1988 | Bonzel |
| 4,917,666 A | 4/1990 | Solar et al. |

(Continued)

FOREIGN PATENT DOCUMENTS

| EP | 1 084 728 | 3/2001 |
| EP | 1 461 108 | 9/2004 |

(Continued)

OTHER PUBLICATIONS

Terumo Corporation Press Release, "New Release of Terumo PTCA Catehter RX-2 (pet name "Ryujin Plus"), a Device for Use in the Treatment of Angina and Myocardial Infarction," Jan. 7, 2005, 2 sheets.

(Continued)

*Primary Examiner* — Jackie Ho
*Assistant Examiner* — Edelmira Bosques
(74) *Attorney, Agent, or Firm* — Seager, Tufte & Wickhem LLC

(57) ABSTRACT

An elongate shaft of a medical catheter including a thermoset polymeric tubular member including a skived distal portion. The skived distal portion includes a distally extending trough having a convex surface and a concave surface. A thermoplastic tubular sleeve may be positioned over at least a portion of the skived distal portion of the thermoset polymeric tubular member. In some instances, the thermoplastic tubular sleeve includes a crescent-shaped tubular portion defining a crescent-shaped lumen. The trough of the skived distal portion may extend through the crescent-shaped lumen. The thermoplastic tubular sleeve is thermally bonded to the inner and outer tubular members of a distal section of the elongate shaft at a guidewire port joint.

19 Claims, 23 Drawing Sheets

(56) References Cited

U.S. PATENT DOCUMENTS

| | | | |
|---|---|---|---|
| 4,998,923 | A | 3/1991 | Samson et al. |
| 5,040,548 | A | 8/1991 | Yock |
| 5,095,915 | A | 3/1992 | Engelson |
| 5,156,594 | A | 10/1992 | Keith |
| 5,217,482 | A | 6/1993 | Keith |
| 5,242,396 | A | 9/1993 | Evard |
| 5,279,562 | A | 1/1994 | Sirhan et al. |
| 5,300,025 | A | 4/1994 | Wantink |
| 5,322,505 | A | 6/1994 | Krause et al. |
| 5,346,505 | A | 9/1994 | Leopold |
| 5,387,193 | A | 2/1995 | Miraki |
| 5,439,447 | A | 8/1995 | Miraki |
| 5,458,613 | A | 10/1995 | Gharibadeh et al. |
| 5,477,856 | A | 12/1995 | Lundquist |
| 5,480,382 | A | 1/1996 | Hammerslag et al. |
| 5,490,837 | A | 2/1996 | Blaeser et al. |
| 5,496,294 | A | 3/1996 | Hergenrother et al. |
| 5,507,751 | A | 4/1996 | Goode et al. |
| 5,507,766 | A | 4/1996 | Kugo et al. |
| 5,522,818 | A | 6/1996 | Keith et al. |
| 5,542,434 | A | 8/1996 | Imran et al. |
| 5,626,593 | A | 5/1997 | Imran |
| 5,634,902 | A | 6/1997 | Johnson et al. |
| 5,658,251 | A | 8/1997 | Ressemann et al. |
| 5,690,613 | A | 11/1997 | Verbeek |
| 5,702,439 | A | 12/1997 | Keith et al. |
| 5,720,724 | A | 2/1998 | Ressemann et al. |
| 5,743,875 | A * | 4/1998 | Sirhan et al. ............ 604/96.01 |
| 5,743,876 | A | 4/1998 | Swanson |
| 5,807,355 | A | 9/1998 | Ramzipoor et al. |
| 5,810,867 | A | 9/1998 | Zarbatany et al. |
| 5,823,995 | A | 10/1998 | Fitzmaurice et al. |
| 5,876,375 | A | 3/1999 | Penny |
| 5,882,336 | A | 3/1999 | Janacek |
| 5,911,715 | A | 6/1999 | Berg et al. |
| 5,957,903 | A | 9/1999 | Mirzaee et al. |
| 5,980,484 | A | 11/1999 | Ressemann et al. |
| 5,980,486 | A | 11/1999 | Enger |
| 6,004,291 | A | 12/1999 | Ressemann et al. |
| 6,013,069 | A | 1/2000 | Sirhan et al. |
| 6,022,343 | A | 2/2000 | Johnson et al. |
| 6,024,722 | A | 2/2000 | Rau et al. |
| 6,030,405 | A | 2/2000 | Zarbatany et al. |
| 6,039,699 | A | 3/2000 | Viera |
| 6,048,338 | A | 4/2000 | Larson et al. |
| 6,066,114 | A | 5/2000 | Goodin et al. |
| 6,066,144 | A | 5/2000 | Wolf et al. |
| 6,102,890 | A | 8/2000 | Stivland et al. |
| 6,129,708 | A | 10/2000 | Enger |
| 6,152,909 | A | 11/2000 | Bagaoisan et al. |
| 6,190,358 | B1 | 2/2001 | Fitzmaurice et al. |
| 6,193,686 | B1 | 2/2001 | Estrada et al. |
| 6,246,914 | B1 | 6/2001 | de la Rama et al. |
| 6,273,879 | B1 | 8/2001 | Keith et al. |
| 6,344,029 | B1 | 2/2002 | Estrada et al. |
| 6,409,863 | B1 | 6/2002 | Williams et al. |
| 6,447,479 | B1 | 9/2002 | Nobuyoshi et al. |
| 6,488,655 | B1 | 12/2002 | Wantink et al. |
| 6,524,300 | B2 | 2/2003 | Meglin |
| 6,533,754 | B1 | 3/2003 | Hisamatsu et al. |
| 6,548,010 | B1 | 4/2003 | Stivland et al. |
| 6,575,958 | B1 | 6/2003 | Happ et al. |
| 6,579,246 | B2 | 6/2003 | Jacobsen et al. |
| 6,589,207 | B1 | 7/2003 | El-Nounou |
| 6,592,569 | B2 | 7/2003 | Bigus et al. |
| 6,605,057 | B2 | 8/2003 | Fitzmaurice et al. |
| 6,623,448 | B2 | 9/2003 | Slater |
| 6,635,029 | B1 | 10/2003 | Venturelli |
| 6,648,854 | B1 * | 11/2003 | Patterson et al. ............ 604/96.01 |
| 6,695,812 | B2 | 2/2004 | Estrada et al. |
| 6,733,487 | B2 | 5/2004 | Keith et al. |
| 6,746,423 | B1 | 6/2004 | Wantink |
| 6,887,219 | B2 | 5/2005 | Wantink |
| 6,890,318 | B2 | 5/2005 | Wantink |
| 7,001,358 | B2 | 2/2006 | Fitzmaurice et al. |
| 7,037,291 | B2 | 5/2006 | Lee et al. |
| 7,169,162 | B2 | 1/2007 | Garakani |
| 7,195,611 | B1 | 3/2007 | Simpson et al. |
| 7,294,124 | B2 | 11/2007 | Eidenschink |
| 7,367,967 | B2 | 5/2008 | Eidenschink |
| 2001/0029362 | A1 | 10/2001 | Sirhan et al. |
| 2001/0037085 | A1 | 11/2001 | Keith et al. |
| 2003/0105427 | A1 | 6/2003 | Lee et al. |
| 2003/0176837 | A1 | 9/2003 | Fitzmaurice et al. |
| 2004/0059292 | A1 | 3/2004 | Hisamatsu et al. |
| 2004/0230178 | A1 | 11/2004 | Wu |
| 2004/0249436 | A1 | 12/2004 | Aznoian et al. |
| 2005/0049552 | A1 | 3/2005 | Holzapfel et al. |
| 2005/0059959 | A1 | 3/2005 | Eidenschink |
| 2006/0064074 | A1 | 3/2006 | Mallaby |
| 2006/0142696 | A1 | 6/2006 | Kumoyama et al. |
| 2007/0135763 | A1 | 6/2007 | Musbach et al. |
| 2007/0142821 | A1 | 6/2007 | Hennessy et al. |
| 2008/0287786 | A1 | 11/2008 | Lentz |

FOREIGN PATENT DOCUMENTS

| | | |
|---|---|---|
| JP | 6-277296 | 10/1994 |
| JP | 8-257128 | 10/1996 |
| JP | 2000-116788 | 4/2000 |
| JP | 2001-095924 | 4/2001 |
| JP | 2001-333984 | 12/2001 |
| JP | 2002-536032 | 10/2002 |
| WO | 00/24451 | 5/2000 |
| WO | 2004/047899 | 6/2004 |
| WO | 2006/007137 | 1/2006 |
| WO | 2006/113912 | 10/2006 |

OTHER PUBLICATIONS

Terumo Corporation Product Sheet, "Heartrail II PTCA Guiding Catheters," dated before Feb. 20, 2009, one sheet.

Terumo Corporation Product Sheet, "Crosswire/Crosswire NT," dated before Feb. 20, 2009, one sheet.

Terumo Corporation Product Sheet, "Runthrough NS PTCA Guide Wire," dated before Feb. 20, 2009, one sheet.

Terumo Corporation Product Sheet, "Ryujin Plus PTCA Dilatation Catheters," dated before Feb. 20, 2009, one sheet.

Terumo Corporation Product Sheet, "Tsunami Coronary Stent," dated before Feb. 20, 2009, one sheet.

* cited by examiner

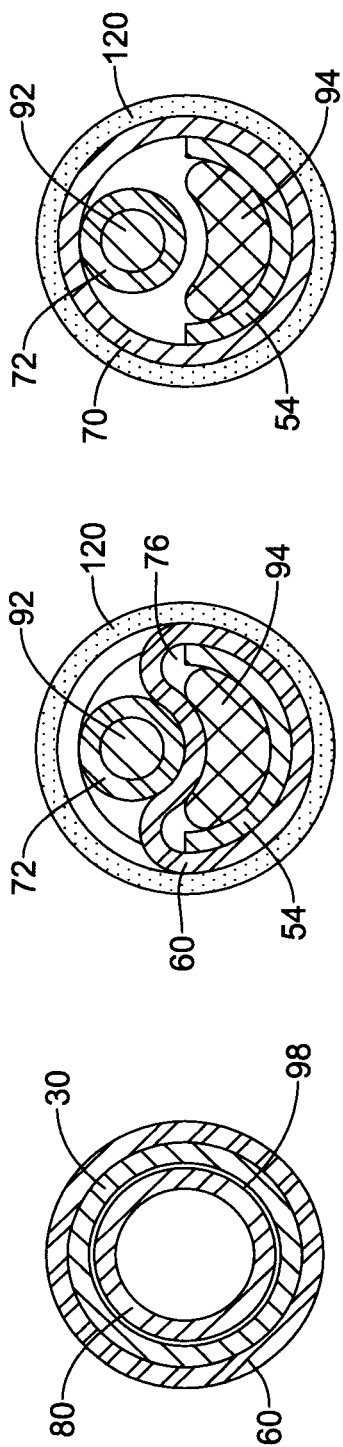

CATHETER WITH SKIVED TUBULAR MEMBER

RELATED APPLICATIONS

This application is a continuation of U.S. application Ser. No. 12/389,393, filed Feb. 20, 2009the disclosure of which is incorporated herein in its entirety.

TECHNICAL FIELD

The disclosure is directed to a catheter including a skived tubular member. More particularly, the disclosure is directed to a skived tubular member of a catheter shaft formed of a thermoset polymer.

BACKGROUND

Single-operator-exchange (SOE) or "monorail" catheters are catheters in which only a distal portion of the catheter tracks over a guidewire. Proximal of the distal portion that tracks the guidewire, the guidewire is located exterior of the catheter shaft. Therefore, the proximal portion of an SOE catheter need not include a guidewire lumen, which would be necessary in an over-the-wire (OTW) catheter construction. An SOE catheter has advantages in that, by not tracking the guidewire over its entire length, the catheter and guidewire are more easily moved relative to one another, such as during a catheter exchange during a medical procedure. One example of an early patent in this area is U.S. Pat. No. 5,156,594 to Keith, the disclosure of which is incorporated herein by reference.

One drawback of SOE catheters is the difficulty of fabrication. Construction of an SOE device typically involves securing several lengths of tubing together such that a distal portion of the SOE catheter includes an additional lumen for receiving a guidewire. A guidewire opening or port is provided to allow a guidewire to be introduced into the guidewire lumen through the guidewire port. A number of different manners of providing the guidewire port joint to a rapid exchange-type of medical device have been suggested, for example, by Fitzmaurice et al., U.S. Pat. No. 6,190,358; Enger, U.S. Pat. No. 5,980,486; Estrada et al., U.S. Pat. No. 6,193,686; and Williams et al., U.S. Pat. No. 6,409,863. U.S. Pat. No. 6,409,863 to Williams is incorporated herein by reference. The disclosure of the Keith patent above, incorporated by reference, discloses a crimped hypotube, which is then adhesively attached to a distal polymer member having a guidewire tube and an outer tube around the guidewire tube.

Another drawback of SOE catheters is the integrity and kink resistance of the elongate shaft proximate the guidewire port joints, as well as the pushability of the various portions of the shaft. Therefore, there is an ongoing need to provide catheter constructions which enhance the performance of the catheter by providing improved pushability and kink resistance to the catheter shaft.

SUMMARY

The disclosure is directed to several alternative designs, materials and methods of manufacturing medical device structures and assemblies.

Accordingly, one illustrative embodiment is a medical catheter including a hub assembly and an elongate shaft extending distally from the hub assembly. The elongate shaft includes a proximal section, a midshaft section, and a distal section. The proximal section includes a metallic hypotube. The midshaft section includes a thermoset polyimide tubular member and a thermoplastic tubular sleeve extending over at least a portion of the thermoset polyimide tubular member. The thermoset polyimide tubular member includes a skived distal portion. The distal section includes an outer tubular member and an inner tubular member disposed within the outer tubular member. The thermoplastic tubular sleeve includes a crescent-shaped tubular portion defining a crescent-shaped lumen. At least a portion of the skived distal portion of the thermoset polyimide tubular member is located within the crescent-shaped lumen of the crescent-shaped tubular portion of the thermoplastic tubular sleeve.

Another illustrative embodiment is a medical catheter including a hub assembly and an elongate shaft extending distally from the hub assembly. The elongate shaft includes a proximal section, a midshaft section, and a distal section. The proximal section includes a tubular member. The midshaft section includes a thermoset polymeric tubular member and a thermoplastic tubular sleeve extending over at least a portion of the thermoset polymeric tubular member. The thermoset polymeric tubular member includes a skived distal portion having a compound cut surface including a first cut surface portion through a wall of the thermoset polymeric tubular member and a second cut surface portion through the wall of the thermoset polymeric tubular member. The first cut surface portion is non-parallel to the second cut surface portion. The distal section includes an outer tubular member and an inner tubular member disposed within the outer tubular member. The skived distal portion of the thermoset polymeric tubular member overlaps a proximal portion of the outer tubular member of the distal section, and a distal portion of the thermoplastic tubular sleeve is thermally bonded to the inner tubular member and the outer tubular member of the distal section. In some instances, the thermoplastic tubular sleeve includes a crescent-shaped tubular portion defining a crescent-shaped lumen, wherein at least a portion of the skived distal portion of the thermoset polymeric tubular member is located within the crescent-shaped lumen of the crescent-shaped tubular portion of the thermoplastic tubular sleeve.

Yet another illustrative embodiment is a method of manufacturing a medical catheter. A thermoset polymeric tubular member is provided. A portion of a distal portion of the thermoset polymeric tubular member is removed to form a skived distal portion of the thermoset polymeric tubular member. A first thermoplastic tubular sleeve is disposed over at least a portion of the thermoset polymeric tubular member including at least a portion of the skived distal portion. The skived distal portion of the thermoset polymeric tubular member is overlapped with an outer tubular member of a distal section of the medical catheter at a junction between the thermoset polymeric tubular member and the outer tubular member. The junction is heated to a temperature greater than a melting temperature of the outer tubular member and greater than a melting temperature of the first thermoplastic tubular sleeve and below a melting temperature of the thermoset polymeric tubular member. Heating of the junction thermally bonds the first thermoplastic tubular sleeve to the outer tubular member. In some instances, a second thermoplastic tubular sleeve is disposed around a proximal portion of the outer tubular member and a distal portion of the first thermoplastic tubular sleeve at the junction. Heating of the junction thermally bonds the second thermoplastic tubular sleeve to each of the first thermoplastic tubular sleeve and the outer tubular member.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 6A is a transverse cross-sectional view of the catheter shaft taken along line 6A-6A of FIG. 6;

FIG. 6B is a transverse cross-sectional view of the catheter shaft taken along line 6B-6B of FIG. 6;

FIG. 6C is a transverse cross-sectional view of the catheter shaft taken along line 6C-6C of FIG. 6;

Figure 1:
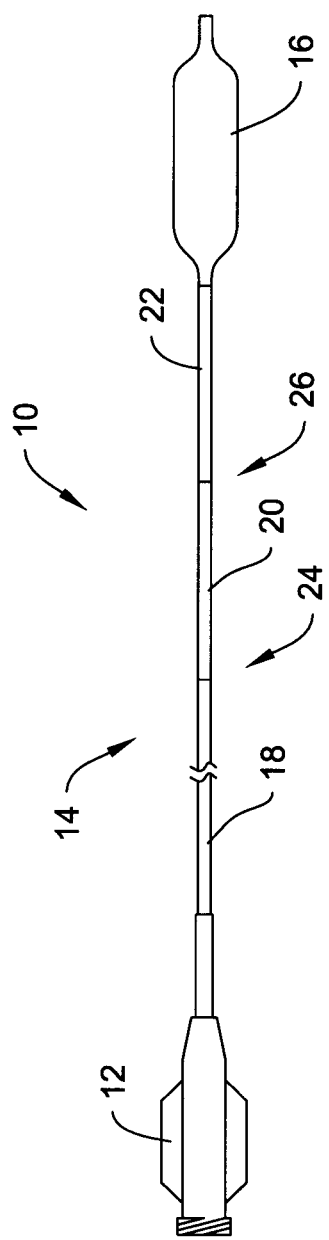
FIG. 1 is a plan view of a medical catheter in accordance with this disclosure.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to the figures, FIG. 1 is a plan view of a medical catheter 10, illustrated as a single operator exchange (SOE) catheter. The catheter 10 can be one of a variety of different catheters, but in some embodiments is an intravascular catheter. Examples of intravascular catheters include balloon catheters, atherectomy catheters, drug delivery catheters, diagnostic catheters and guide catheters. As illustrated, FIG. 1 portrays the catheter 10 as a balloon catheter. Although the catheter 10 is illustrated as a balloon catheter, in some instances the catheter 10 can be configured for other medical purposes.

The catheter 10 may include a hub assembly 12 and an elongate shaft 14 extending distally from the hub assembly 12. In embodiments in which the catheter 10 is a balloon catheter, the catheter 10 may include a balloon 16, or other inflatable member, secured to a distal portion of the elongate shaft 14. In some embodiments, the balloon 16 may include one or more cutting elements for cutting or scoring a stenosis. In other embodiments, the catheter 10 may additionally or alternatively include one or more other treatment devices or arrangements on a distal portion of the elongate shaft 14.

The elongate shaft 14 may include a proximal shaft section 18, a midshaft section 20, and/or a distal shaft section 22. The elongate shaft 14, in some embodiments, may include additional shaft sections or regions, or fewer shaft sections or regions, if desired. In some embodiments, the proximal shaft section 18 may be secured to the hub assembly 12 and extend distally therefrom, a proximal portion of the midshaft section 20 may be secured to a distal portion of the proximal shaft section 18 and extend distally therefrom, and a proximal portion of the distal shaft section 22 may be secured to a distal portion of the midshaft section 20 and extend distally therefrom. The catheter 10 may include a proximal joint 24 between the proximal shaft section 18 and the midshaft section 20 where the midshaft section 20 is joined with the proximal shaft section 18. The catheter 10 may additionally include a guidewire port joint 26 between the midshaft section 20 and the distal shaft section 22 where the distal shaft section 22 is joined with the midshaft section 20. The guidewire port joint 26 may provide access to a guidewire lumen extending through the distal shaft section 22 of the catheter 10.

Figure 2:
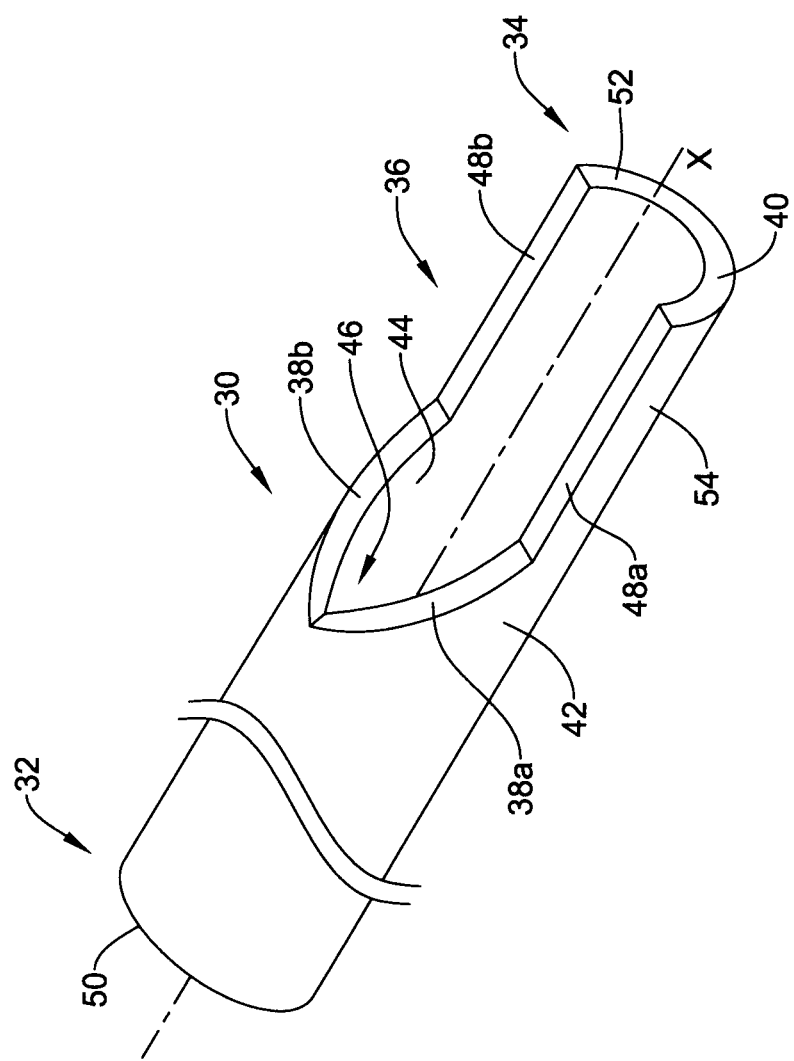
FIG. 2 is a perspective view of a skived tubular member for use in a catheter shaft section of the medical catheter of FIG. 1.

FIG. 2 is a perspective view of a skived tubular member 30 which may be provided in the midshaft section 20 of the elongate shaft 14. The skived tubular member 30 may be formed of a thermoset polymeric material, such as a thermoset polyimide, in some embodiments. In other embodiments, however, the skived tubular member 30 may be formed of another relatively stiff material, such as a metallic hypotube. The skived tubular member 30 may provide the midshaft section 20 with a degree of rigidity in order to enhance the pushability of the midshaft section 20 of the elongate shaft 14.

Figure 2A:
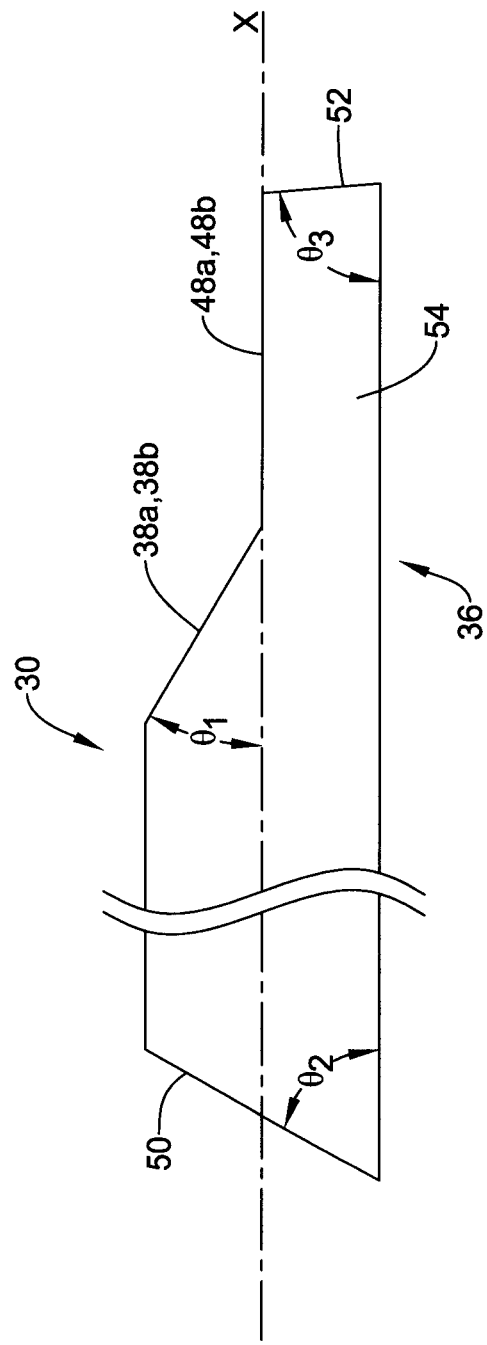
FIG. 2A is a side view of the skived tubular member of FIG. 2.

The skived tubular member 30 may have a proximal end 32 and a distal end 34. The distal portion of the skived tubular member 30 may be skived or cut to provide the skived tubular member 30 with a distal skived portion 36. In some embodiments, as shown in FIG. 2, the distal skived portion 36 may be a compound skive portion including multiple cut surfaces or edges. FIG. 2A, which is a side view of the skived tubular member 30, and FIG. 2B, which is a distal end view of the skived tubular member 30, further illustrate one possible configuration of the compound nature of the distal skived portion 36 of the skived tubular member 30.

For example, the distal skived portion 36 may include first cut surfaces 38a, 38b cut through the tubular wall 40 of the skived tubular member 30 at a first angle $\theta_1$ to the central longitudinal axis X of the skived tubular member 30. The first cut surfaces 38a, 38b may each extend along a plane which transects the skived tubular member 30 at the angle $\theta_1$ to the central longitudinal axis X. In some embodiments, the angle $\theta_1$ may be an oblique angle, such as an acute angle, or a perpendicular angle to the central longitudinal axis X. In some embodiments, the angle $\theta_1$ may be between above 0° to about 90°, between about 3° to about 60°, between about 3° to about 45°, between about 5° to about 90°, between about 15° to about 90°, between about 15° to about 60°, between about 15° to about 45°, between about 25° to about 35°, or about 30° to the central longitudinal axis X.

The first cut surfaces 38a, 38b may extend across the wall 40 of the skived tubular member 30 from the outer surface 42 of the skived tubular member 30 to the inner surface 44 of the skived tubular member 30 which defines a lumen 46 extending through the skived tubular member 30.

The distal skived portion 36 may include second cut surfaces 48a, 48b cut through the tubular wall 40 of the skived tubular member 30. The second cut surfaces 48a, 48b may each extend along a plane which is non-parallel to a plane which each of the first cut surfaces 38a, 38b extend along. In some embodiments, the second cut surfaces 48a, 48b may be parallel to the central longitudinal axis X of the skived tubular member 30. However, in other embodiments, the second cut surfaces 48a, 48b may be at an angle to the central longitudinal axis X, such as an oblique angle to the central longitudinal axis X. Thus, the second cut surfaces 48a, 48b may be non-parallel to the first cut surfaces 38a, 38b.

The second cut surfaces 48a, 48b may extend across the wall 40 of the skived tubular member 30 from the outer surface 42 of the skived tubular member 30 to the inner surface 44 of the skived tubular member 30 which defines a lumen 46 extending through the skived tubular member 30.

In some embodiments, the proximal end surface 50 may be perpendicular to the central longitudinal axis X of the skived tubular member 30, or the proximal end surface 50 may be at an oblique angle, such as an acute angle, to the central longitudinal axis X. As shown in FIG. 2A, in some embodiments, the proximal end surface 50 may be at an angle $\theta_2$. In some embodiments, the angle $\theta_2$ may be between above 0° to about 90°, between about 3° to about 90°, between about 30° to about 90°, between about 45° to about 75°, between about 60° to about 90°, between about 60° to about 85°, between about 45° to about 60°, between about 30° to about 75°, between about 30° to about 60°, about 30°, about 45°, or about 60° to the central longitudinal axis X. In some embodiments, the proximal end surface 50 may be a stepped surface having a first proximal surface portion lying in a first plane transverse (e.g., perpendicular) to the longitudinal axis X and a second proximal surface portion lying in a second plane transverse (e.g., perpendicular) to the longitudinal axis X, wherein the first plane is nonplanar with the second plane. For example, the first proximal surface portion may be located proximal of the second proximal surface portion, in which the first proximal surface portion may be parallel or nonparallel to the second proximal surface portion.

In some embodiments, the distal end surface 52 may be perpendicular to the central longitudinal axis X of the skived tubular member 30, or the distal end surface 52 may be at an oblique angle, such as an acute angle, to the central longitudinal axis X. As shown in FIG. 2A, in some embodiments, the distal end surface 52 may be at an angle $\theta_3$. In some embodiments, the angle $\theta_3$ may be between about 30° to about 90°, between about 45° to about 75°, between about 60° to about 90°, between about 60° to about 85°, between about 45° to about 60°, between about 30° to about 75°, between about 30° to about 60°, about 30°, about 45°, about 60°, or about 75° to the central longitudinal axis X.

Figure 2B:
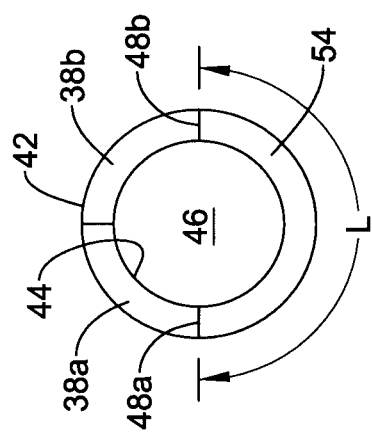
FIG. 2B is a distal end view of the skived tubular member of FIG. 2.

The distal skived portion 36 of the skived tubular member 30 may define a trough 54 of the arcuate portion of the tubular wall 40 remaining subsequent the skiving process, exposing the lumen 46 of the skived tubular member 30. The outer surface 42 of the skived tubular member 30 may define a convex surface of the trough 54, and the inner surface 44 of the skived tubular member 30 may define a concave surface of the trough 54. As shown in FIG. 2B, the trough 54 may extend through an arc length L less than the circumference of the skived tubular member 30. For instance, in some embodiments the arc length of the trough 54 may be less than 330°, less than 240°, less than 210°, less than 180°, less than 150°, less than 120°, or less than 90°. In some embodiments the arc length of the trough 54 may be between about 30° to about 330°, between about 120° and about 240°, between about 150° to about 210°, or about 180°.

Figure 3:
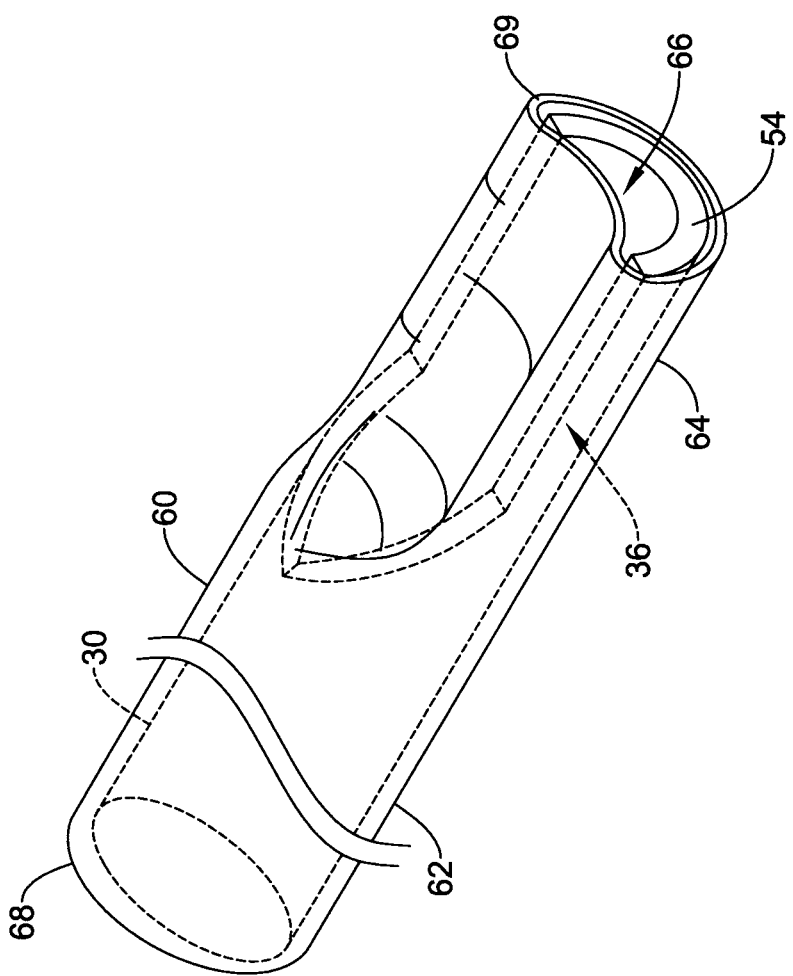
FIG. 3 is a perspective view of a tubular sleeve positioned over the skived tubular member of FIG. 2.

As shown in FIG. 3, in some embodiments, the midshaft section 20 may include a tubular sleeve 60 disposed over or around at least a portion of the skived tubular member 30 (shown in phantom lines). For example, the tubular sleeve 60 may surround at least a portion of the distal skived portion 36 of the skived tubular member 30. As shown in FIG. 3, the tubular sleeve 60 may extend over the entire, or substantially the entire, length of the skived tubular member 30 in some embodiments. The tubular sleeve 60 may be desirably formed of a thin, thermoplastic polymeric material. Some example materials may include, but are not limited to, polyamide, polyether block amide, polyurethane, silicone rubber, nylon, polyethylene, fluorinated hydrocarbon polymers, and the like. For example, in some particular examples the sleeve 60 is 100% polyamide 6, polyamide 12, or thermoplastic polyurethane. Some polymer materials suitable for use in the sleeve 60 are sold under the trademarks of PEBAX, PELLETHANE, TEXIN and VESTAMID.

In some embodiments, the tubular sleeve 60 may include a proximal circular tubular portion 62 and a distal crescent-shaped tubular portion 64 defining a crescent-shaped lumen 66. The crescent-shaped portion 64 may be molded or otherwise formed in the tubular sleeve 60 during a manufacturing process The crescent-shaped portion 64 may be formed in the tubular sleeve 60 either prior to or subsequent to positioning the tubular sleeve 60 over the skived tubular member 30. The crescent-shaped portion 64 may have a convex outer surface portion and a concave outer surface portion.

In some embodiments the skived tubular member 30 may be positioned such that at least a portion of the skived distal portion 36 of the skived tubular member 30 is located within the crescent-shaped lumen 66 of the crescent-shaped tubular portion 64 of the tubular sleeve 60. In some embodiments, the trough 54 of the distal skived portion 36 may extend distal of the distal end of the tubular sleeve 60, while in other embodiments, the trough 54 of the distal skived portion 36 may terminate within the crescent-shaped lumen 66. FIG. 3B illustrates an end view of the tubular sleeve 60 with the trough 54 of the distal skived portion 36 positioned in the crescent-shaped lumen 66. The convex surface of the trough 54 may face, contact or rest against a concave portion of the crescent-shaped lumen 66, while a convex portion of the crescent-shaped lumen 66 may extend toward or into the opening through the wall 40 of the skived distal portion created when material is removed from the skived tubular member 30 to form the distal skived portion 36.

The tubular sleeve 60 may be positioned over the skived tubular member 30 in a variety of ways. For example, the skived tubular member 30 may be pre-formed and then the tubular sleeve 60 may be slid over the skived tubular member 30 and optionally secured in place, such as by thermal tacking or adhesive, if desired. In other embodiments, the tubular sleeve 60 may be first extruded, then expanded slightly, such as during a blowing process, to arrange the molecular chains of the tubular sleeve 60 in a circumferential orientation. The tubular sleeve 60 may then be positioned over the pre-formed skived tubular member 30. Once placed over the skived tubular member 30, the tubular sleeve 60 may be heated in order that the tubular sleeve 60 may contract or compress around the skived tubular member 30 to secure the tubular sleeve 60 to the skived tubular member 30.

Figure 3A:
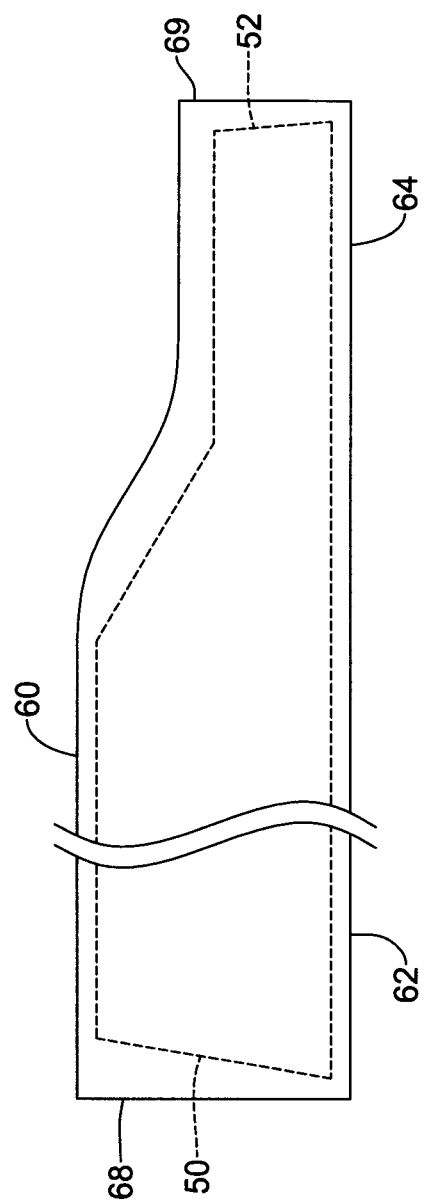
FIG. 3A is a side view of the tubular sleeve of FIG. 3 with the skived tubular member located therein.
Figure 3B:
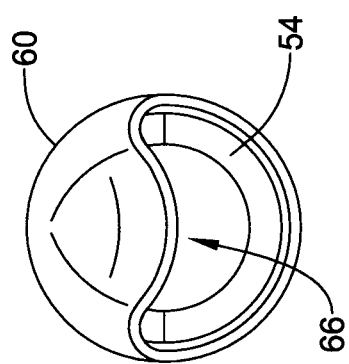
FIG. 3B is a distal end view of the tubular sleeve of FIG. 3 with the skived tubular member located therein.

In some embodiments, as shown in FIG. 3A, the proximal end 68 of the tubular sleeve 60 may be located at the proximal end surface 50 or proximal of the proximal end surface 50 of the skived tubular member 30. Furthermore, as shown in FIG. 3A, the distal end 69 of the tubular sleeve 60 may be located at the distal end surface 52 or distal of the distal end surface 52 of the skived tubular member 30 in some embodiments. In other embodiments, the tubular sleeve 60 may terminate distal of the proximal end surface 50 of the skived tubular member 30 and/or may terminate proximal of the distal end surface 52 of the skived tubular member 30.

FIGS. 4 through 11 illustrate several embodiments of manufacturing the elongate shaft 14 of the catheter 10 including the skived tubular member 30 discussed above in regard to FIG. 2.

Figure 4:
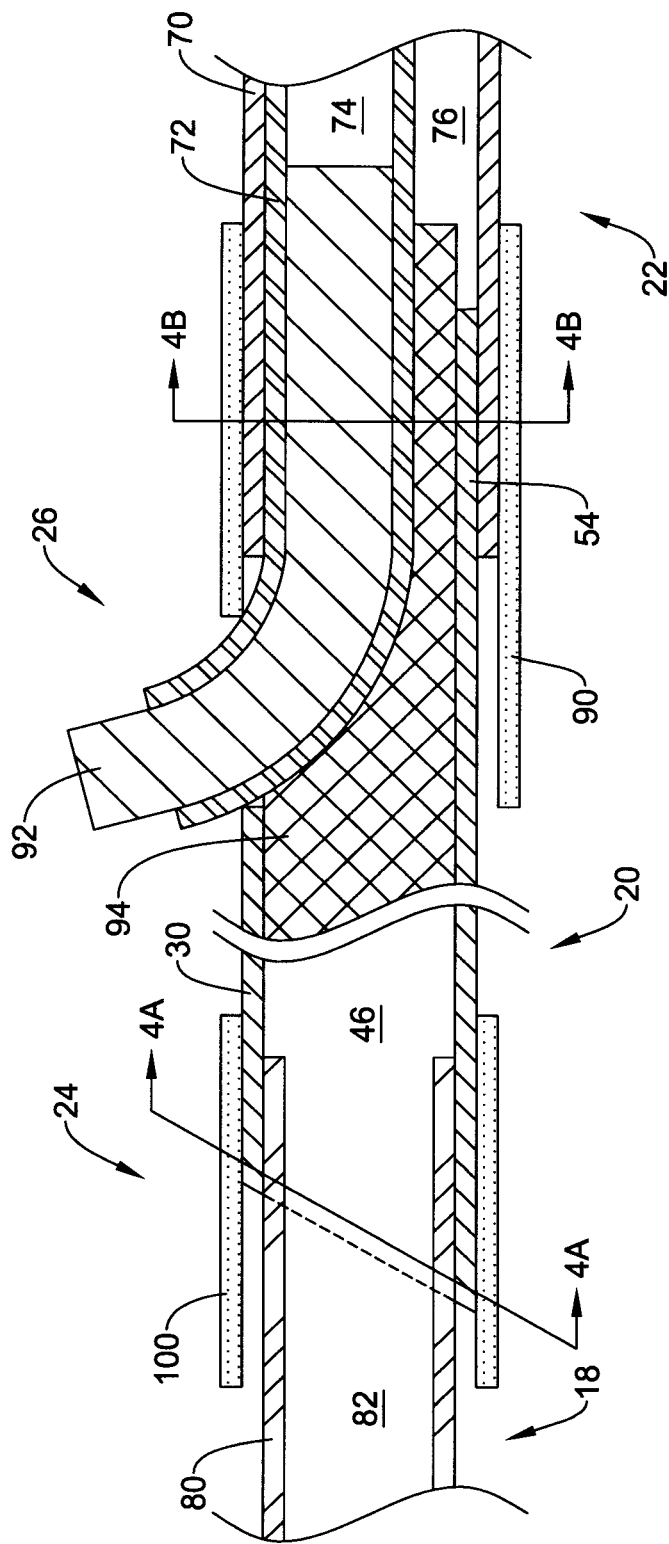
FIG. 4 is a longitudinal cross-sectional view of a first embodiment of a proximal joint region and a guidewire port joint region of the catheter shaft of FIG. 1 prior to heating the joint regions.
Figure 5:
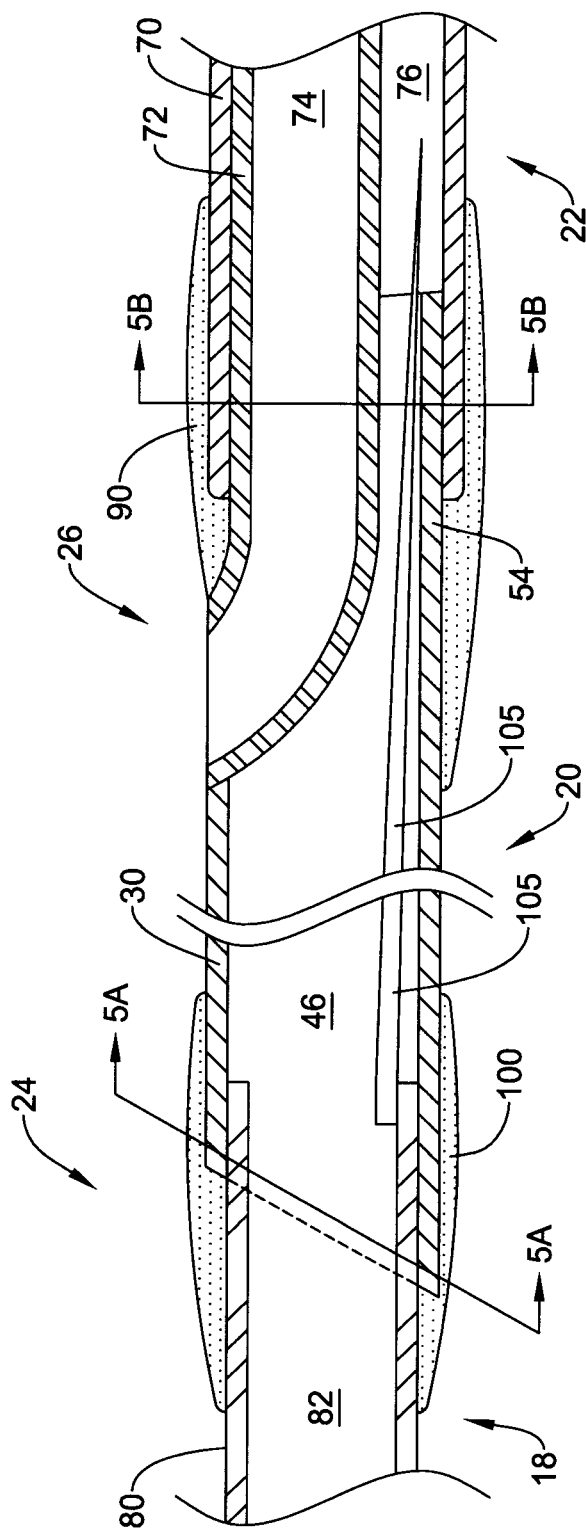
FIG. 5 is a longitudinal cross-sectional view of the joint regions of the catheter shaft shown in FIG. 4 subsequent to heating the joint regions.

FIGS. 4 and 5 illustrate a first embodiment of the elongate shaft 14 utilizing the skived tubular member 30, prior to heating portions of the elongate shaft 14 (FIG. 4) and subsequent to heating portions of the elongate shaft 14 (FIG. 5).

As shown in FIG. 4, the midshaft section 20 may include the skived tubular member 30 extending distally from the proximal joint 24 to the guidewire port joint 26. The skived tubular member 30 may be secured to the proximal section 18 proximate the proximal joint 24 and may be secured to the distal section 22 proximate the guidewire port joint 26.

The distal section 22 of the elongate shaft 14 may include an outer tubular member 70 and an inner tubular member 72 extending through the outer tubular member 70. The inner tubular member 72 may define a guidewire lumen 74 configured to receive a guidewire therethrough. A guidewire (not shown), extending through the guidewire lumen 74, may pass through the distal section 22 of the elongate shaft 14 and then exterior to the elongate shaft 14 at the guidewire port joint 26. The space between the outer surface of the inner tubular member 72 and the inner surface of the outer tubular member 70 may define an inflation lumen 76 in fluid communication with the balloon 16 to deliver an inflation fluid to the balloon 16 in order to inflate the balloon 16 during a medical procedure. The inflation lumen 76 may be in fluid communication with the lumen 46 of the skived tubular member 30.

The inner tubular member 72 may include and/or be made of any of a broad variety of materials and/or structures. The inner tubular member 72 may have a single-layer tubular construction or a multi-layer tubular construction, or a combination thereof. For example, the inner tubular member 72 may be a single tubular member formed by a single layer of material, or in other embodiments, may be formed by a plurality of tubular members and/or a plurality of layers of material that may be the same and/or different, but in combination form the inner tubular member 72. In yet other embodiments, some portions of the inner tubular member 72 can include a single layer construction, while other portions may include a multi-layer construction. U.S. Pat. No. 6,319,228 to Kastenhofer, incorporated herein by reference, discloses one possible multi-layer tubular member having an inner layer, an outer layer and an intermediate layer which may be used as the inner tubular member 72.

In some embodiments, the inner layer of the inner tubular member 72 may include a lubricious polymer such as high density polyethylene (HDPE) or polytetrafluoroethylene (PTFE), for example, or a copolymer of tetrafluoroethylene with perfluoroalkyl vinyl ether (PFA) (more specifically, perfluoropropyl vinyl ether or perfluoromethyl vinyl ether), or the like. In some particular embodiments, the inner layer is formed of Marlex® HDPE, which can extend the length of the inner tubular member 72.

Furthermore, in some embodiments, the outer layer of the inner tubular member 72 may include a flexible polymer, for example a polymer material having a durometer in the range of about 5D to about 90D. For example, the outer layer can include or be made up of one or more tubular segments of a polyamide, such as polyamide 12, polyether block amide (PEBA), a polyether-ester elastomer, or other similar material.

In some embodiments, the intermediate layer, which may be considered a tie layer in some instances, securing the inner layer to the outer layer, may be a low density polyethylene (LDPE), such as a modified LDPE.

In one particular embodiment, the inner tubular member 72 may be a co-extruded three-layer shaft segment including an inner layer of high density polyethylene (HDPE, namely Marlex® 4903), an outer layer of polyether block amide (PEBA, namely Pebax® 7233) and a tie-layer of Plexar® 380 to adhere the layers. Plexar® 380 is a known commercially available tie layer material which is a modified low density polyethylene.

The outer tubular member 70 may be formed of any desired polymer material, such as a thermoplastic polymer. For instance, some suitable thermoplastic materials include polyamide, such as polyamide 6, polyamide 12, or polyamide 612, and polyether block amide (PEBA). In one particular embodiment, the outer tubular member 70 may be a PEBA having a durometer hardness of 70D (e.g., Pebax® 7033). Other suitable polymer materials include those listed above regarding the inner tubular member 72.

Further, as shown in FIGS. 4 and 5, a proximal portion of the skived tubular member 30 may be secured to a proximal tubular member 80 of the proximal section 18 of the elongate shaft 14. The lumen 82 of the proximal tubular member 80 may be in fluid communication with the lumen 46 of the skived tubular member 30, providing a fluid pathway through the elongate shaft 14 to the balloon 16.

The proximal tubular member 80 may be formed of any suitable material. In some embodiments, the proximal tubular member 80 of the proximal section 18 may be a metallic tubular member, such as a hypotube, which may in some embodiments include a series of cuts therealong to provide the metallic tubular member 80 with a desired degree of lateral bending. Some examples of suitable metals and metal alloys can include stainless steel, such as 304V, 304L, and 316L stainless steel; nickel-titanium alloy such as a superelastic (i.e., pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it may be desirable to use metals, or metal alloys that are suitable for metal joining techniques such as welding, soldering, brazing, crimping, friction fitting, adhesive bonding, etc.

In other embodiments, the proximal tubular member 80 may be formed of a polymeric material. Some examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyether-ester, polymer/metal composites, etc., or mixtures, blends or combinations thereof.

As shown in FIG. 4, in assembling the elongate shaft 14, the skived tubular member 30 may be joined to the outer and inner tubular members 70, 72 at the guidewire port joint 26. For instance, at least a portion of the distal skived portion 36 may be overlapped with a proximal portion of the outer tubular member 70 of the distal section 22. For example, the distal skived portion 36 of the skived tubular member 30 may be inserted into the outer tubular member 70, for example into the lumen 76 defined between the inner tubular member 72 and the outer tubular member 70. The inner tubular member 72 may extend proximally out of the outer tubular member 70 and generally follow the profile of the distal skived portion 36.

A tubular sleeve 90 may be placed around a proximal portion of the outer tubular member 72 and a distal portion of the skived tubular member 30 to bridge the interface between the skived tubular member 30 and the outer tubular member 70 at the guidewire point joint 26.

The tubular sleeve 90 may be desirably formed of a thin, thermoplastic polymeric material, similar to the tubular sleeve 60 discussed above. Some example materials may include, but are not limited to, polyamide, polyether block amide, polyurethane, silicone rubber, nylon, polyethylene, fluorinated hydrocarbon polymers, and the like. For example, in some particular examples the sleeve 60 is 100% polyamide 6, polyamide 12, or thermoplastic polyurethane. Some polymer materials suitable for use in the tubular sleeve 90 are sold under the trademarks of PEBAX, PELLETHANE, TEXIN and VESTAMID.

Also shown in FIG. 4, during the manufacturing process, a mandrel 92 may be inserted into the inner tubular member 72 to maintain the shape of the guidewire lumen 74 throughout the manufacturing process. Furthermore, a mandrel 94 (also shown in FIG. 4), which may include a crescent-shaped portion, may be inserted into the lumen 46 of the skived tubular member 30 and into the inflation lumen 76 defined between the inner tubular member 72 and the outer tubular member 70 of the distal section 22 to maintain the shape of the inflation lumen 76.

Figure 4B:
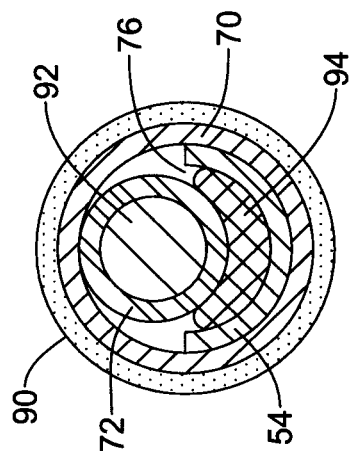
FIG. 4B is a transverse cross-sectional view of the catheter shaft taken along line 4B-4B of FIG. 4.

FIG. 4B illustrates a transverse cross-sectional view taken along line 4B-4B of FIG. 4, illustrating the arrangement of components prior to heating the guidewire port joint 26 during a manufacturing step. As can be seen from FIG. 4B, the trough 54 of the distal skived portion 36 of the skived tubular member 30 is positioned in the outer tubular member 70 such that the convex surface of the trough 54 faces the inner surface of the outer tubular member 70 and the crescent-shaped portion of the mandrel 94 rests against the concave surface of the trough 54, between the inner tubular member 72 and the trough 54.

During a subsequent step in manufacturing the elongate shaft 14, the guidewire port joint 26 may be heated to an elevated temperature, such as greater than the melting temperature of the tubular sleeve 90. The guidewire port joint 26 may be heated by any desired heating means, for instance, laser, hot jaw or hot air, to thermally bond the thermoplastic components proximate the guidewire port joint 26. It is noted that although not shown in the drawings, during heating of the guidewire port joint 26, a length of heat shrink tubing, such as a length of polyolefin heat shrink tubing, may be placed around the sleeve 90 and adjacent portions of the elongate shaft 14 to aid in the heating process. Subsequent to heating the guidewire port joint 26, the heat shrink tubing may be removed.

In embodiments in which the skived tubular member 30 is a thermoset polymer member (e.g., thermoset polyimide), the guidewire port joint 26 may be heated to a temperature greater than the melting temperature of the tubular sleeve 90, but below a melting temperature of the skived tubular member 30. Furthermore, in heating the guidewire port joint 26, the guidewire port joint 26 may be heated to a temperature greater than the melting temperatures of each of the outer tubular member 70 and the inner tubular member 72 (e.g., at least one or more layers of the inner tubular member 72).

Figure 5B:
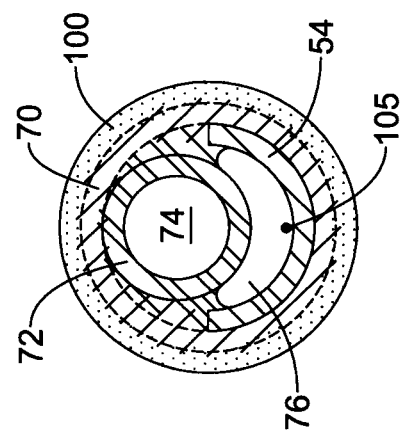
FIG. 5B is a transverse cross-sectional view of the catheter shaft taken along line 5B-5B of FIG. 5.

Molten material of the tubular sleeve 90 may surround the skived tubular member 30, the outer tubular member 70 and the portion of the inner tubular member 72 extending from the outer tubular member 70 along the distal skived portion 36 of the skived tubular member 30. When heat is removed and the guidewire port joint 26 is allowed to cool, polymeric material of the tubular sleeve 90, as shown in FIGS. 5 and 5B, can be seen surrounding a portion of the skived tubular member 30 as well as a portion of the outer tubular member 70 and the portion of the inner tubular member 72 extending out from the outer tubular member 70, sealing the guidewire port joint 26.

Furthermore, molten material of the outer tubular member 70 and the inner tubular member 72 may flow around a portion of the trough 54 of the distal skived portion 36 of the skived tubular member 30 such that polymeric material of the outer tubular member 70 and/or the inner tubular member 72 contacts the concave surface of the trough 54 as well as the convex surface of the trough 54, encapsulating the trough 54 of the skived tubular member 30 in the thermoplastic material of the outer tubular member 70 and/or the inner tubular member 72. Encapsulation of the trough 54 such that thermoplastic material of the outer tubular member 70 and/or the inner tubular member 72 resides on each of the convex surface and the concave surface of the trough 54 may help secure the skived tubular member 30 to the distal section 22 of the elongate shaft 14, preventing deflection of the trough 54 during catheter bending. Thus, the skived tubular member 30 may be secured to the outer tubular member 70 and the inner tubular member 72 without melting the skived tubular member 30 and/or using an adhesive.

Additionally, subsequent to heating the guidewire port joint 26, the mandrels 92, 94 may be removed from the lumens 74, 76, and the excess portion of the inner tubular member 72 which extends outward from the outer surface of the skived tubular member 30 may be trimmed away as shown in FIG. 5.

In a further manufacturing step, a core wire 105, such as a metallic core wire may be secured to the distal portion of the proximal tubular member 80, such as by welding or adhesively bonding the core wire 105 to the proximal tubular member 80. The core wire 105 may extend distally through the lumen 46 of the skived tubular member 30 to and/or across the guidewire port joint 26. In some instances, the core wire 105 may extend distal of the distal end of the skived tubular member 30 into the inflation lumen 76 defined between the inner tubular member 72 and the outer tubular member 70 of the distal section 22.

Turning now to the proximal joint 24 shown in FIG. 4, the proximal tubular member 80 may be joined to the skived tubular member 30 using a tubular sleeve 100. The tubular sleeve 100 may be desirably formed of a thin, thermoplastic polymeric material, similar to the tubular sleeve 60 discussed above. Some example materials may include, but are not limited to, polyamide, polyether block amide, polyurethane, silicone rubber, nylon, polyethylene, fluorinated hydrocarbon polymers, and the like. For example, in some particular examples the sleeve 60 is 100% polyamide 6, polyamide 12, or thermoplastic polyurethane. Some polymer materials suitable for use in the tubular sleeve 100 are sold under the trademarks of PEBAX, PELLETHANE, TEXIN and VESTAMID.

As shown in FIG. 4, a proximal portion of the skived tubular member 30 may be overlapped with a distal portion of the proximal tubular member 80, forming a lap joint between the skived tubular member 30 and the proximal tubular member 80. In other embodiments, however, the distal end of the proximal tubular member 80 may abut the proximal end of the skived tubular member 30, forming a butt joint. As shown, a distal portion of the proximal tubular member 80 may be inserted into the lumen 46 of the skived tubular member 30. The tubular sleeve 100 may be positioned over the lap joint such that a portion of the tubular sleeve 100 is located around the proximal tubular member 80 and a portion of the tubular sleeve 100 is located around the skived tubular member 30.

In the embodiment shown in FIG. 4, the proximal end surface 50 of the skived tubular member 30 may be tapered at an oblique angle relative to the central longitudinal axis X of the skived tubular member 30. It is noted however, that in other embodiments the proximal end surface 50 of the skived tubular member 30 may be perpendicular to the central longitudinal axis X.

Figure 4A:
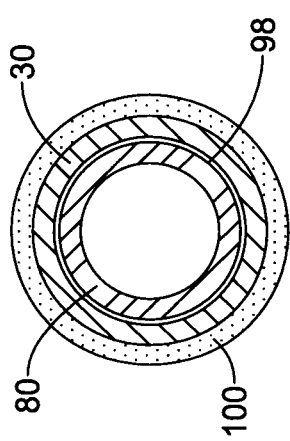
FIG. 4A is a transverse cross-sectional view of the catheter shaft taken along line 4A-4A of FIG. 4.

A clearance fit between the inner surface of the skived tubular member 30 and the outer surface of the proximal tubular member 80 may be provided to allow insertion of the distal portion of the proximal tubular member 80 into the proximal portion of the skived tubular member 30. FIG. 4A illustrates a gap 98 (exaggerated for the purposes of illustration) between the inner surface of the skived tubular member 30 and the outer surface of the proximal tubular member 80 provided by the clearance fit between the skived tubular member 30 and the proximal tubular member 80. In some embodiments, the nominal difference between the inner diameter of the skived tubular member 30 and the outer diameter of the proximal tubular member 80 may be about 0.001 inches to about 0.002 inches, thus the gap 98 may be about 0.0005 to about 0.001 inches.

During a subsequent step in manufacturing the elongate shaft 14, the proximal joint 24 may be heated to an elevated temperature, such as greater than the melting temperature of the tubular sleeve 100. Heating of the proximal joint 24 may be performed concurrently with or separate from heating the guidewire port joint 26. The proximal joint 24 may be heated by any desired heating means, for instance, laser, hot jaw or hot air. It is noted that although not shown in the drawings, during heating of the proximal joint 24, a length of heat shrink tubing, such as a length of polyolefin heat shrink tubing, may be placed around the sleeve 100 and adjacent portions of the elongate shaft 14 to aid in the heating process. Subsequent to heating the proximal joint 24, the heat shrink tubing may be removed.

Figure 5A:
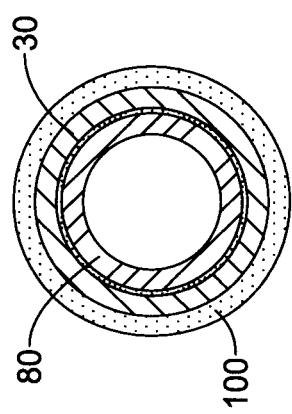
FIG. 5A is a transverse cross-sectional view of the catheter shaft taken along line 5A-5A of FIG. 5.

In embodiments in which the proximal tubular member 80 is a metallic tubular member (e.g., hypotube) and the skived tubular member 30 is a thermoset polymer member (e.g., thermoset polyimide), the proximal joint 24 may be heated to a temperature greater than the melting temperature of the tubular sleeve 100, but below a melting temperature of the proximal tubular member 80 and below a melting temperature of the skived tubular member 30. When the tubular sleeve 100 is heated above its melting temperature, the molten material of the tubular sleeve 100 may flow around the outer surface of the proximal tubular member 80 and the skived tubular member 30. Tapering the proximal end surface 50 of the skived tubular member 30 creates a greater surface area for the thermoplastic material of the tubular sleeve 100 to contact the interface between the proximal tubular member 80 and the skived tubular member 30. Furthermore, by tapering the proximal end surface 50 of the skived tubular member 30, polymeric material of the tubular sleeve 100 may also flow into the gap 98 between the inner surface of the skived tubular member 30 and the outer surface of the proximal tubular member 80. Radial forces exerted on the molten polymer of the tubular sleeve 100 by the heat shrink tubing may help force molten material of the tubular sleeve 100 into the gap 98. When heat is removed and the proximal joint 24 is allowed to cool, polymeric material of the tubular sleeve 100, as shown in FIGS. 5 and 5A, can be seen surrounding a portion of the proximal tubular member 80 and the skived tubular member 30, as well as located in the gap 98 between the inner surface of the skived tubular member 30 and the outer surface of the proximal tubular member 80. The polymeric material of the tubular sleeve 100 located in the gap 98 between the proximal tubular member 80 and the skived tubular member 30 provides a component of shear stress as well as tensile stress necessary to be overcome in order to separate the proximal tubular member 80 and the skived tubular member 30, resulting in a stronger joint.

Figure 6:
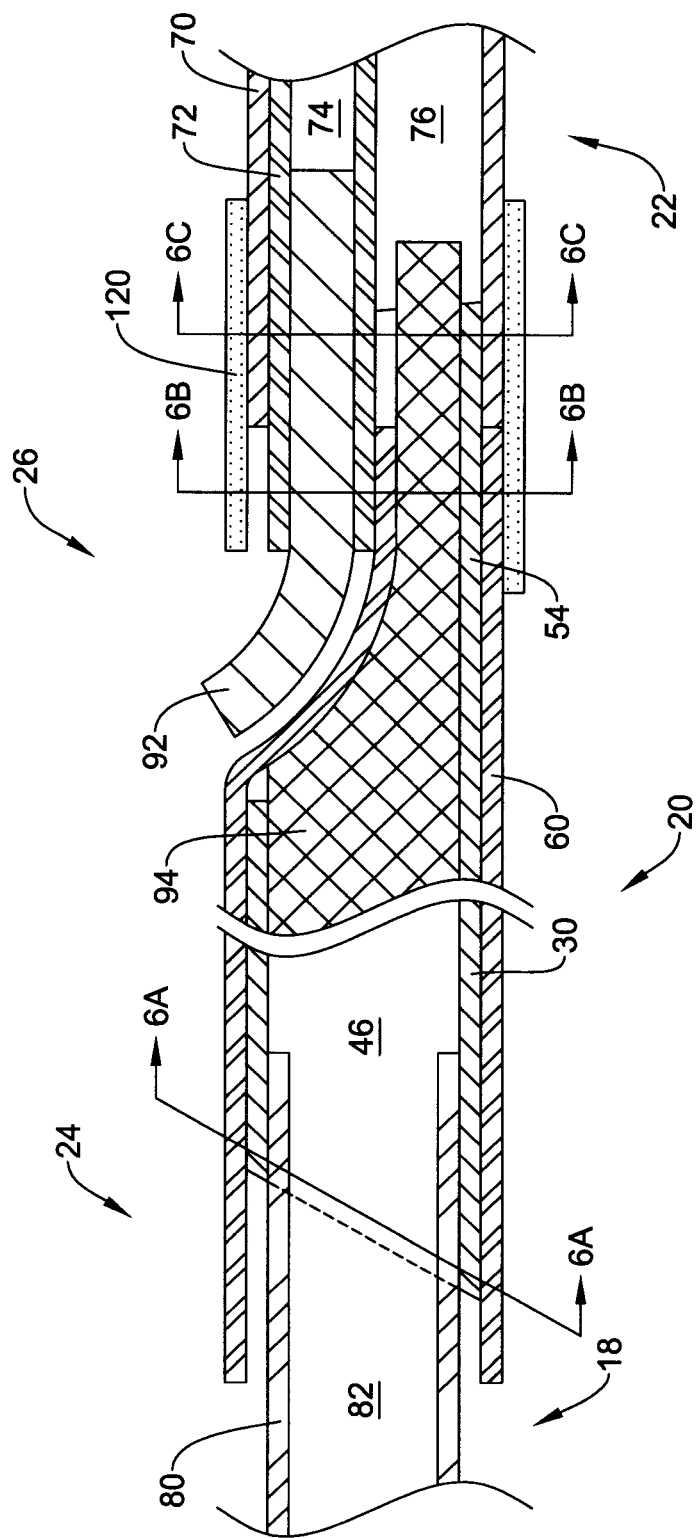
FIG. 6 is a longitudinal cross-sectional view of a second embodiment of a proximal joint region and a guidewire port joint region of the catheter shaft of FIG. 1 prior to heating the joint regions.
Figure 7:
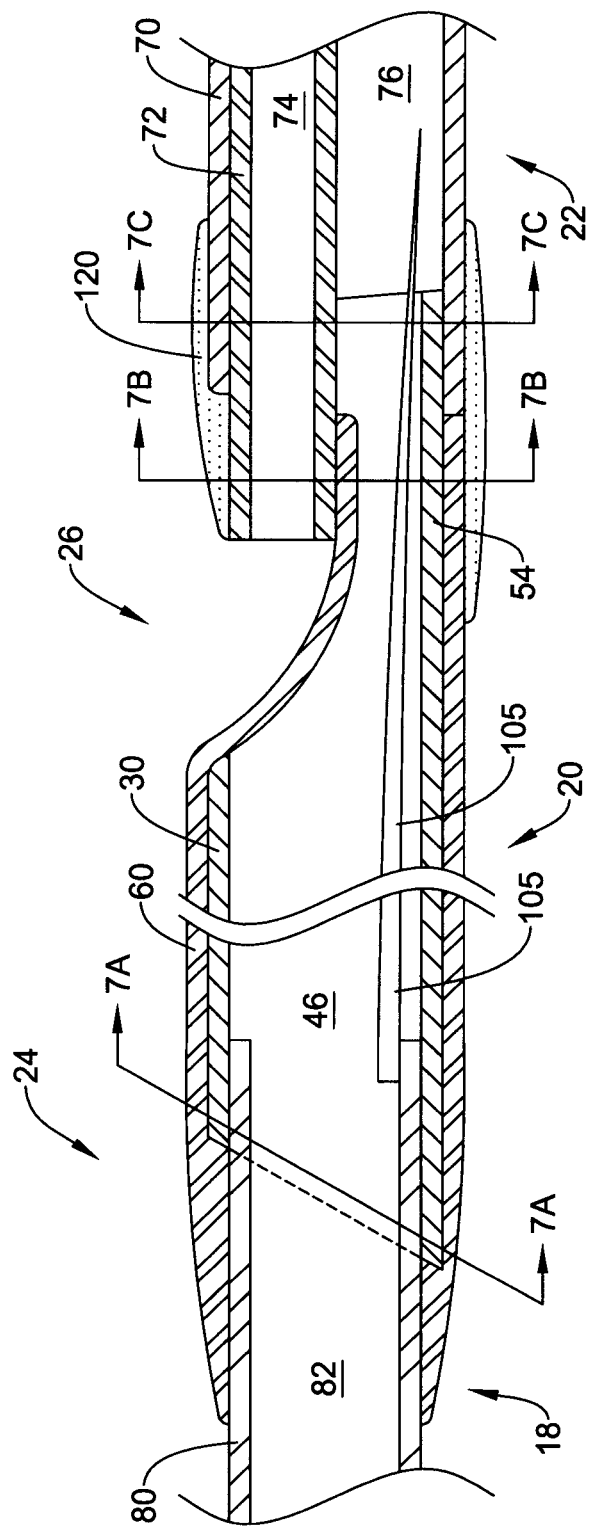
FIG. 7 is a longitudinal cross-sectional view of the joint regions of the catheter shaft shown in FIG. 6 subsequent to heating the joint regions.

FIGS. 6 and 7 illustrate a second embodiment of the elongate shaft 14 utilizing the skived tubular member 30, prior to heating portions of the elongate shaft 14 (FIG. 6) and subsequent to heating portions of the elongate shaft 14 (FIG. 7).

Similar to the embodiment shown in FIGS. 4 and 5, the proximal section 18 of the elongate shaft 14 may include a proximal tubular member 80 as described above. Furthermore, the distal section 22 of the elongate shaft 14 may include an outer tubular member 70 and an inner tubular member 72 extending through the outer tubular member 70 as described above.

As shown in FIG. 6, the midshaft section 20 may include the skived tubular member 30 extending distally from the proximal joint 24 to the guidewire port joint 26. The skived tubular member 30 may be secured to the proximal section 18 proximate the proximal joint 24 and may be secured to the distal section 22 proximate the guidewire port joint 26. The midshaft section 20 may also include the tubular sleeve 60, shown in FIG. 3, extending over the entire length or substantially the entire length of the skived tubular member 30. As shown, the tubular sleeve 60 may extend from a location proximal of the proximal end surface 50 of the skived tubular member 30 to the distal skived portion 36 of the skived tubular member 30. A portion of the trough 54 of the skived tubular member 30 may extend distally from the tubular sleeve 60.

A proximal portion of the skived tubular member 30 may be secured to the proximal tubular member 80 and a distal portion of the skived tubular member 30 may be secured to the outer tubular member 70 and/or the inner tubular member 72. Furthermore, as discussed herein, the tubular sleeve 60 may be secured to the proximal tubular member 80 and a distal portion of the tubular sleeve 60 may be secured to the outer tubular member 70 and the inner tubular member 72.

The lumen 46 of the skived tubular member 30 may be in fluid communication with each of the lumen 82 of the proximal tubular member 80 and the inflation lumen 76 defined between the inner tubular member 72 and the outer tubular member 70 of the distal section 22.

As shown in FIG. 6, in assembling the elongate shaft 14, the skived tubular member 30 may be joined to the outer and inner tubular members 70, 72 at the guidewire port joint 26. For instance, at least a portion of the distal skived portion 36 may be overlapped with a proximal portion of the outer tubular member 70 of the distal section 22. For example, at least a portion of the distal skived portion 36 of the skived tubular member 30 may be inserted into the outer tubular member 70, for example into the lumen 76 defined between the inner tubular member 72 and the outer tubular member 70. The inner tubular member 72 may extend proximally out of the outer tubular member 70.

Furthermore, the distal end of the tubular sleeve 60 may abut the proximal end of the outer tubular member 70, forming a butt joint between the tubular sleeve 60 and the outer tubular member 70. A distal portion of the trough 54 of the skived tubular member 30 may extend distal of the butt joint into the outer tubular member 70. Additionally, a proximal portion of the inner tubular member 72 may face, contact or rest against the concave outer surface of the crescent-shaped portion 64 of the tubular sleeve 60.

A second tubular sleeve 120 may be placed around a proximal portion of the outer tubular member 72 and a distal portion of the tubular sleeve 60 to bridge the interface between the tubular sleeve 60 and the outer tubular member 70 at the guidewire point joint 26.

The second tubular sleeve 120 may be desirably formed of a thin, thermoplastic polymeric material, similar to the tubular sleeve 60 discussed above. Some example materials may include, but are not limited to, polyamide, polyether block amide, polyurethane, silicone rubber, nylon, polyethylene, fluorinated hydrocarbon polymers, and the like. For example, in some particular examples the sleeve 60 is 100% polyamide 6, polyamide 12, or thermoplastic polyurethane. Some polymer materials suitable for use in the second tubular sleeve 120 are sold under the trademarks of PEBAX, PELLETHANE, TEXIN and VESTAMID.

Also shown in FIG. 6, during the manufacturing process, a mandrel 92 may be inserted into the inner tubular member 72 to maintain the shape of the guidewire lumen 74 throughout the manufacturing process. Furthermore, a mandrel 94 (also shown in FIG. 6), which may include a crescent-shaped portion, may be inserted into the lumen 46 of the skived tubular member 30, into the crescent-shaped lumen 66 of the tubular sleeve 60, and into the inflation lumen 76 defined between the inner tubular member 72 and the outer tubular member 70 of the distal section 22 to maintain the shape of the crescent-shaped lumen 66 and the inflation lumen 76.

FIG. 6B illustrates a transverse cross-sectional view taken along line 6B-6B of FIG. 6, illustrating the arrangement of components prior to heating the guidewire port joint 26 during a manufacturing step. As can be seen from FIG. 6B, both the crescent-shaped portion 64 of the sleeve 60 and the trough 54 of the skived tubular member 30 are surrounded by the second tubular sleeve 120, with the trough 54 located within the crescent-shaped lumen 66 of the tubular sleeve 60. Furthermore, the outer surface of the inner tubular member 72 may face, contact and/or rest against the concave outer surface of the crescent-shaped portion 64 of the tubular sleeve 60. Additionally, the crescent-shaped portion of the mandrel 94 is shown positioned between the concave surface of the trough 54 and the convex inner surface of the crescent-shaped portion 64 of the tubular sleeve 60.

FIG. 6C illustrates a transverse cross-sectional view taken along line 6C-6C of FIG. 6, illustrating the arrangement of components prior to heating the guidewire port joint 26 during a manufacturing step. As can be seen from FIG. 6C, a distal portion of the trough 54 of the distal skived portion 36 of the skived tubular member 30, extending distal of the tubular sleeve 60, is positioned in the outer tubular member 70 such that the convex surface of the trough 54 faces the inner surface of the outer tubular member 70 and the crescent-shaped portion of the mandrel 94 rests against the concave surface of the trough 54, between the inner tubular member 72 and the trough 54.

During a subsequent step in manufacturing the elongate shaft 14, the guidewire port joint 26 may be heated to an elevated temperature, such as greater than the melting temperature of each of the tubular sleeve 60 and the second sleeve 120. The guidewire port joint 26 may be heated by any desired heating means, for instance, laser, hot jaw or hot air, to thermally bond the thermoplastic components proximate the guidewire port joint 26. It is noted that although not shown in the drawings, during heating of the guidewire port joint 26, a length of heat shrink tubing, such as a length of polyolefin heat shrink tubing, may be placed around the sleeve 120 and adjacent portions of the elongate shaft 14 at the guidewire port joint 26 to aid in the heating process. Subsequent to heating the guidewire port joint 26, the heat shrink tubing may be removed.

In embodiments in which the skived tubular member 30 is a thermoset polymer member (e.g., thermoset polyimide), the guidewire port joint 26 may be heated to a temperature greater than the melting temperature of the tubular sleeve 60 and the second sleeve 120, but below a melting temperature of the skived tubular member 30. Furthermore, in heating the guidewire port joint 26, the guidewire port joint 26 may be heated to a temperature greater than the melting temperatures of each of the outer tubular member 70 and the inner tubular member 72 (e.g., at least one or more layers of the inner tubular member 72).

Molten material of the second tubular sleeve 120 may surround the tubular sleeve 60 and the outer tubular member 70, bridging across the interface (e.g., butt joint) between the distal end of the tubular sleeve 60 and the proximal end of the outer tubular member 70. When heat is removed and the guidewire port joint 26 is allowed to cool, polymeric material of the tubular sleeve 120, as shown in FIGS. 7, 7B and 7C, can be seen surrounding a portion of the tubular sleeve 60, as well as a portion of the outer tubular member 70 and the portion of the inner tubular member 72 extending out from the outer tubular member 70, thermally bonding the tubular sleeve 60 to the outer tubular member 70.

Figure 7C:
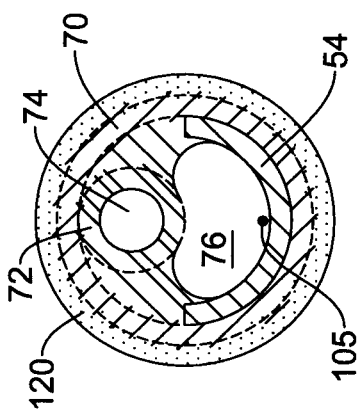
FIG. 7C is a transverse cross-sectional view of the catheter shaft taken along line 7C-7C of FIG. 7.
Figure 7B:
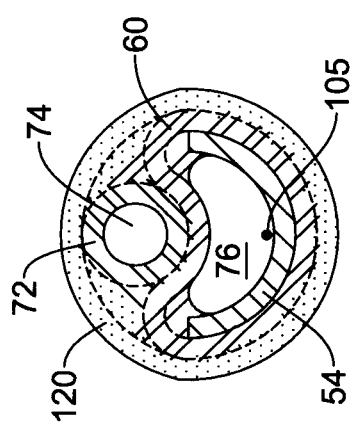
FIG. 7B is a transverse cross-sectional view of the catheter shaft taken along line 7B-7B of FIG. 7.

Additionally, as shown in FIG. 7B, molten material of the tubular sleeve 60 may surround the crescent-shaped portion of the mandrel 94 and the trough 54 of the distal skived portion 36, while melding with the molten material of the inner tubular member 72, encapsulating the trough 54 of the skived tubular member in the thermoplastic material of the tubular sleeve 60, such that thermoplastic material of the tubular sleeve 60 resides on each of the convex surface and the concave surface of the trough 54 to help secure the skived tubular member 30 proximate the guidewire port joint 26.

Furthermore, as shown in FIG. 7C, molten material of the outer tubular member 70 and the inner tubular member 72 may flow around a portion of the trough 54 of the distal skived portion 36 of the skived tubular member 30 extending distally of the tubular sleeve 60 such that polymeric material of the outer tubular member 70 and/or the inner tubular member 72 contacts the concave surface of the trough 54 as well as the convex surface of the trough 54, encapsulating the trough 54 of the skived tubular member 30 in the thermoplastic material of the outer tubular member 70 and/or the inner tubular member 72. Encapsulation of the trough 54 such that thermoplastic material of the outer tubular member 70 and/or the inner tubular member 72 resides on each of the convex surface and the concave surface of the trough 54 helps secure the skived tubular member 30 to the distal section 22 of the elongate shaft 14. Thus, the skived tubular member 30 may be secured to the outer tubular member 70 and the inner tubular member 72 without melting the skived tubular member 30 and/or using an adhesive.

Additionally, subsequent to heating the guidewire port joint 26, the mandrels 92, 94 may be removed from the lumens 74, 76.

In a further manufacturing step, a core wire 105, such as a metallic core wire may be secured to the distal portion of the proximal tubular member 80, such as by welding or adhesively bonding the core wire 105 to the proximal tubular member 80. The core wire 105 may extend distally through the lumen 46 of the skived tubular member 30 to and/or across the guidewire port joint 26. In some instances, the core wire 105 may extend distal of the distal end of the skived tubular member 30 into the inflation lumen 76 defined between the inner tubular member 72 and the outer tubular member 70 of the distal section 22.

Turning now to the proximal joint 24 shown in FIG. 6, the proximal tubular member 80 may be joined to the skived tubular member 30 such that a proximal portion of the tubular sleeve 60 extends over the junction between the proximal tubular member 80 and the skived tubular member 30.

As shown in FIG. 6, a proximal portion of the skived tubular member 30 may overlap a distal portion of the proximal tubular member 80, forming a lap joint between the skived tubular member 30 and the proximal tubular member 80. In other embodiments, however, the distal end of the proximal tubular member 80 may abut the proximal end of the skived tubular member 30, forming a butt joint. As shown, a distal portion of the proximal tubular member 80 may be inserted into the lumen 46 of the skived tubular member 30. The proximal portion of the tubular sleeve 60 may extend proximally over the lap joint such that a portion of the tubular sleeve 60 is located around the proximal tubular member 80 and a portion of the tubular sleeve 60 is located around the skived tubular member 30.

In the embodiment shown in FIG. 6, the proximal end surface 50 of the skived tubular member 30 may be tapered at an oblique angle relative to the central longitudinal axis X of the skived tubular member 30. It is noted however, that in other embodiments the proximal end surface 50 of the skived tubular member 30 may be perpendicular to the central longitudinal axis X.

A clearance fit between the inner surface of the skived tubular member 30 and the outer surface of the proximal tubular member 80 may be provided to allow insertion of the distal portion of the proximal tubular member 80 into the proximal portion of the skived tubular member 30. FIG. 6A illustrates a gap 98 (exaggerated for the purposes of illustration) between the inner surface of the skived tubular member 30 and the outer surface of the proximal tubular member 80 provided by the clearance fit between the skived tubular member 30 and the proximal tubular member 80. In some embodiments, the nominal difference between the inner diameter of the skived tubular member 30 and the outer diameter of the proximal tubular member 80 may be about 0.001 inches to about 0.002 inches, thus the gap 98 may be about 0.0005 to about 0.001 inches.

During a subsequent step in manufacturing the elongate shaft 14, the proximal joint 24 may be heated to an elevated temperature, such as greater than the melting temperature of the tubular sleeve 60. Heating of the proximal joint 24 may be performed concurrently with or separate from heating the guidewire port joint 26. The proximal joint 24 may be heated by any desired heating means, for instance, laser, hot jaw or hot air. It is noted that although not shown in the drawings, during heating of the proximal joint 24, a length of heat shrink tubing, such as a length of polyolefin heat shrink tubing, may be placed around the tubular sleeve 60 and adjacent portions of the elongate shaft 14 to aid in the heating process. Subsequent to heating the proximal joint 24, the heat shrink tubing may be removed.

Figure 7A:
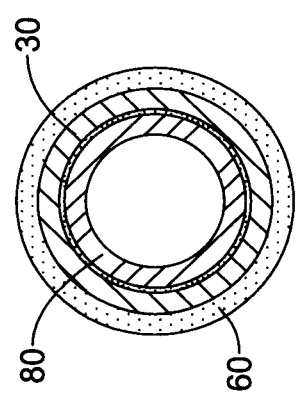
FIG. 7A is a transverse cross-sectional view of the catheter shaft taken along line 7A-7A of FIG. 7.

In embodiments in which the proximal tubular member 80 is a metallic tubular member (e.g., hypotube) and the skived tubular member 30 is a thermoset polymer member (e.g., thermoset polyimide), the proximal joint 24 may be heated to a temperature greater than the melting temperature of the tubular sleeve 60, but below a melting temperature of the proximal tubular member 80 and below a melting temperature of the skived tubular member 30. When the tubular sleeve 60 is heated above its melting temperature, the molten material of the tubular sleeve 60 may flow around the outer surface of the proximal tubular member 80 and the skived tubular member 30. Tapering the proximal end surface 50 of the skived tubular member 30 creates a greater surface area for the thermoplastic material of the tubular sleeve 60 to contact the interface between the proximal tubular member 80 and the skived tubular member 30. Furthermore, by tapering the proximal end surface 50 of the skived tubular member 30, polymeric material of the tubular sleeve 60 may also flow into the gap 98 between the inner surface of the skived tubular member 30 and the outer surface of the proximal tubular member 80. Radial forces exerted on the molten polymer of the tubular sleeve 60 by the heat shrink tubing may help force molten material of the tubular sleeve 60 into the gap 98. When heat is removed and the proximal joint 24 is allowed to cool, polymeric material of the tubular sleeve 60, as shown in FIGS. 7 and 7A, can be seen surrounding a portion of the proximal tubular member 80 and the skived tubular member 30, as well as located in the gap 98 between the inner surface of the skived tubular member 30 and the outer surface of the proximal tubular member 80. The polymeric material of the tubular sleeve 60 located in the gap 98 between the proximal tubular member 80 and the skived tubular member 30 provides a component of shear stress as well as tensile stress necessary to be overcome in order to separate the proximal tubular member 80 and the skived tubular member 30, resulting in a stronger joint.

Figure 8:
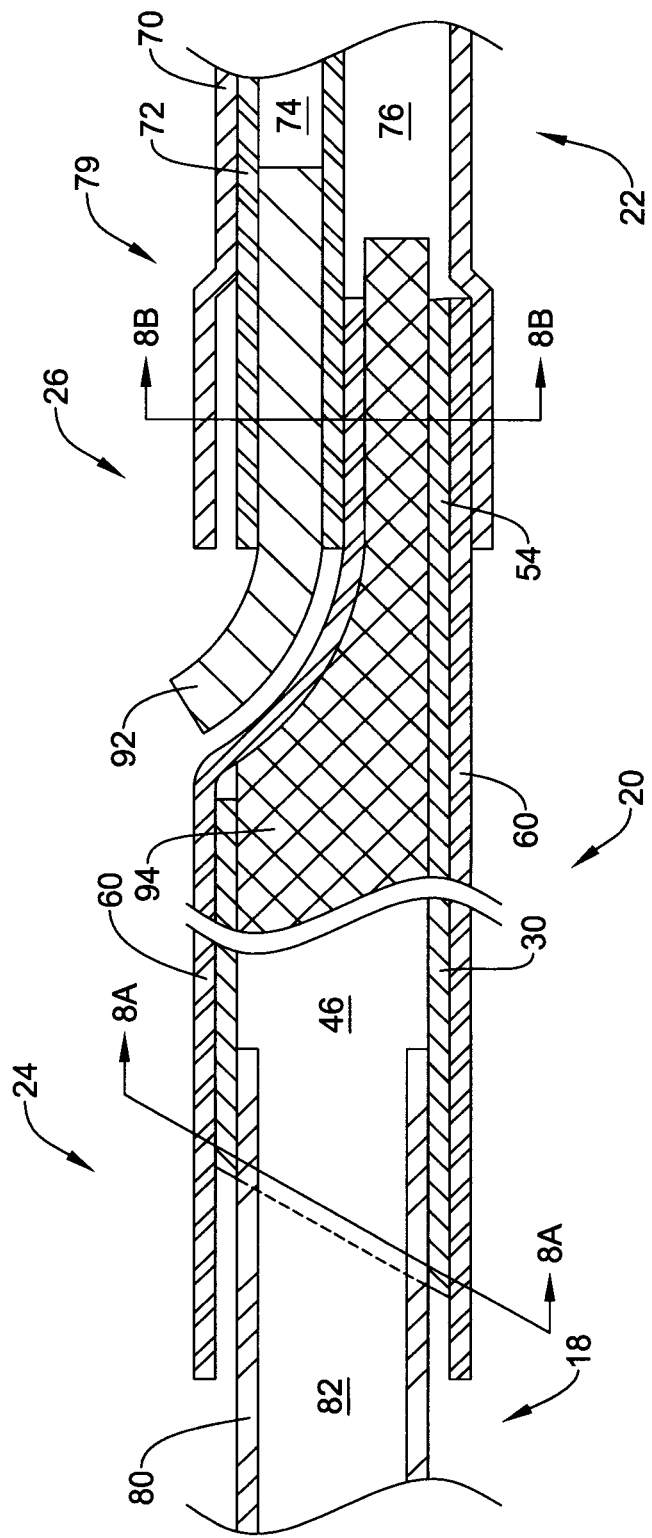
FIG. 8 is a longitudinal cross-sectional view of a third embodiment of a proximal joint region and a guidewire port joint region of the catheter shaft of FIG. 1 prior to heating the joint regions.
Figure 9:
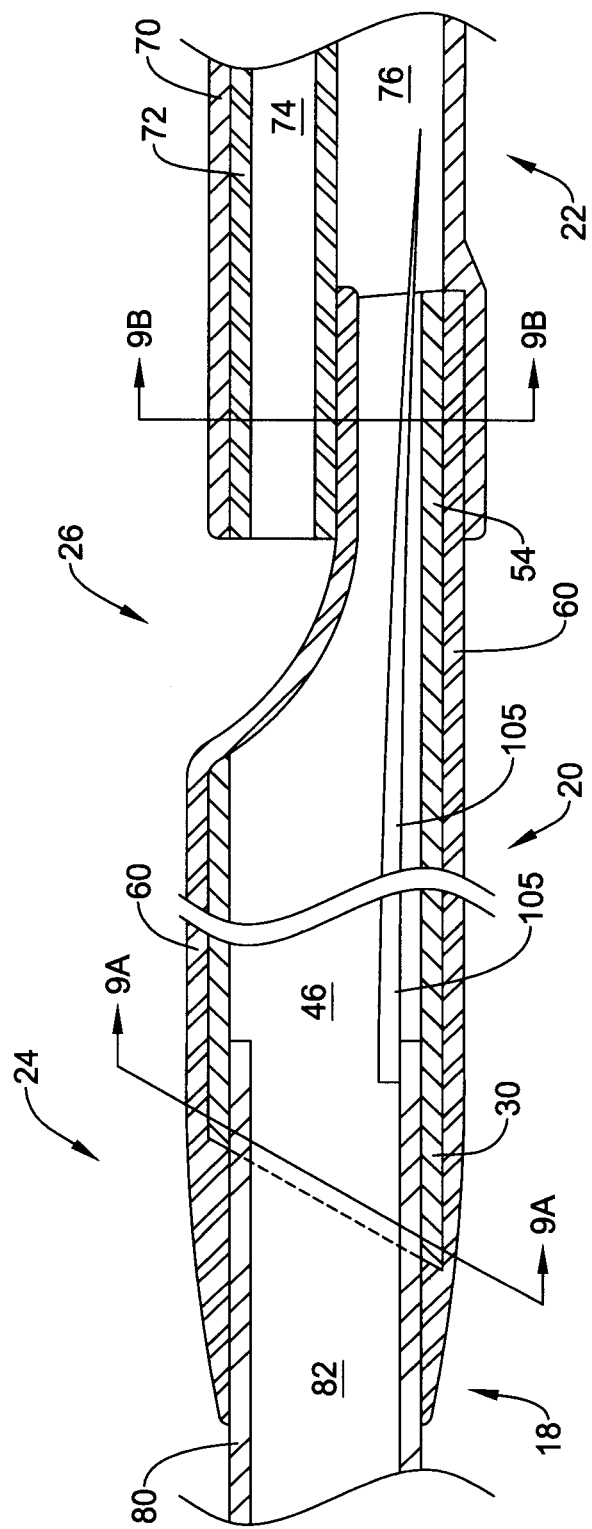
FIG. 9 is a longitudinal cross-sectional view of the joint regions of the catheter shaft shown in FIG. 8 subsequent to heating the joint regions.

FIGS. 8 and 9 illustrate a third embodiment of the elongate shaft 14 utilizing the skived tubular member 30, prior to heating portions of the elongate shaft 14 (FIG. 8) and subsequent to heating portions of the elongate shaft 14 (FIG. 9).

Similar to the embodiment shown in FIGS. 4 and 5, the proximal section 18 of the elongate shaft 14 may include a proximal tubular member 80 as described above. Furthermore, the distal section 22 of the elongate shaft 14 may include an outer tubular member 70 and an inner tubular member 72 extending through the outer tubular member 70 as described above.

As shown in FIG. 8, the midshaft section 20 may include the skived tubular member 30 extending distally from the proximal joint 24 to the guidewire port joint 26. The skived tubular member 30 may be secured to the proximal section 18 proximate the proximal joint 24 and may be secured to the distal section 22 proximate the guidewire port joint 26. The midshaft section 20 may also include the tubular sleeve 60, shown in FIG. 3, extending over the entire length or substantially the entire length of the skived tubular member 30. As shown, the tubular sleeve 60 may extend from a location proximal of the proximal end surface 50 of the skived tubular member 30 to the distal skived portion 36 of the skived tubular member 30. The distal end of the tubular sleeve 60 may extend to the distal end surface 52 or distally of the distal end surface 52 of the skived tubular member 30.

A proximal portion of the skived tubular member 30 may be secured to the proximal tubular member 80 and a distal portion of the skived tubular member 30 may be secured to the outer tubular member 70 and/or the inner tubular member 72. Furthermore, as discussed herein, the tubular sleeve 60 may be secured to the proximal tubular member 80 and a distal portion of the tubular sleeve 60 may be secured to the outer tubular member 70 and the inner tubular member 72.

The lumen 46 of the skived tubular member 30 may be in fluid communication with each of the lumen 82 of the proximal tubular member 80 and the inflation lumen 76 defined between the inner tubular member 72 and the outer tubular member 70 of the distal section 22.

As shown in FIG. 8, in assembling the elongate shaft 14, the skived tubular member 30 may be joined to the outer and inner tubular members 70, 72 at the guidewire port joint 26. For instance, at least a portion of the distal skived portion 36 may be overlapped with a proximal portion of the outer tubular member 70 of the distal section 22. For example, at least a portion of the distal skived portion 36 of the skived tubular member 30 may be inserted into a flared proximal portion 79 of the outer tubular member 70, for example into the lumen 76 defined between the inner tubular member 72 and the outer tubular member 70. In some embodiments, the inner tubular member 72 may extend proximally out of the outer tubular member 70, may terminate at the proximal end of the outer tubular member 70, or may terminate distal of the proximal end of the outer tubular member 70.

Furthermore, a distal portion of the crescent-shaped portion 64 of the tubular sleeve 60, surrounding the trough 54 of the skived tubular member 30, may be positioned in the flared proximal portion 79 of the outer tubular member 70. The distal portion of the crescent-shaped portion 64 may be positioned between the inner surface of the flared proximal portion 79 of the outer tubular member 70 and an outer surface of the inner tubular member 72. Thus, a proximal portion of the inner tubular member 72 may face, contact or rest against the concave outer surface of the crescent-shaped portion 64 of the tubular sleeve 60, with the crescent-shaped portion 64 positioned in the inflation lumen 76 defined between the outer tubular member 70 and the inner tubular member 72.

Also shown in FIG. 8, during the manufacturing process, a mandrel 92 may be inserted into the inner tubular member 72 to maintain the shape of the guidewire lumen 74 throughout the manufacturing process. Furthermore, a mandrel 94 (also shown in FIG. 8), which may include a crescent-shaped portion, may be inserted into the lumen 46 of the skived tubular member 30, into the crescent-shaped lumen 66 of the tubular sleeve 60, and into the inflation lumen 76 defined between the inner tubular member 72 and the outer tubular member 70 of the distal section 22 to maintain the shape of the crescent-shaped lumen 66 and the inflation lumen 76.

Figure 8B:
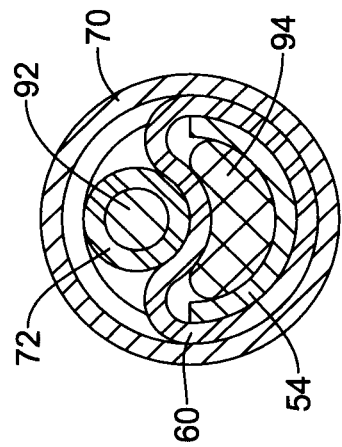
FIG. 8B is a transverse cross-sectional view of the catheter shaft taken along line 8B-8B of FIG. 8.
Figure 8A:
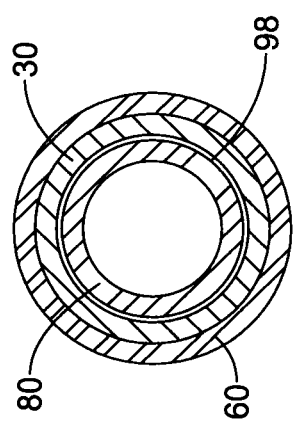
FIG. 8A is a transverse cross-sectional view of the catheter shaft taken along line 8A-8A of FIG. 8.

FIG. 8B illustrates a transverse cross-sectional view taken along line 8B-8B of FIG. 8, illustrating the arrangement of components prior to heating the guidewire port joint 26 during a manufacturing step. As can be seen from FIG. 8B, the trough 54 of the skived tubular member 30 is located within the crescent-shaped lumen 66 of the tubular sleeve 60, with both the crescent-shaped portion 64 of the sleeve 60 and the trough 54 of the skived tubular member 30 disposed in the outer tubular member 70. Furthermore, the outer surface of the inner tubular member 72 may face, contact and/or rest against the concave outer surface of the crescent-shaped portion 64 of the tubular sleeve 60. Additionally, the crescent-shaped portion of the mandrel 94 is shown positioned between the concave surface of the trough 54 and the convex inner surface of the crescent-shaped portion 64 of the tubular sleeve 60.

During a subsequent step in manufacturing the elongate shaft 14, the guidewire port joint 26 may be heated to an elevated temperature, such as greater than the melting temperature of the tubular sleeve 60. The guidewire port joint 26 may be heated by any desired heating means, for instance, laser, hot jaw or hot air, to thermally bond the thermoplastic components proximate the guidewire port joint 26. It is noted that although not shown in the drawings, during heating of the guidewire port joint 26, a length of heat shrink tubing, such as a length of polyolefin heat shrink tubing, may be placed around the sleeve 60 and outer tubular member 70, and adjacent portions of the elongate shaft 14 at the guidewire port joint 26 to aid in the heating process. Subsequent to heating the guidewire port joint 26, the heat shrink tubing may be removed.

In embodiments in which the skived tubular member 30 is a thermoset polymer member (e.g., thermoset polyimide), the guidewire port joint 26 may be heated to a temperature greater than the melting temperature of the tubular sleeve 60, but below a melting temperature of the skived tubular member 30. Furthermore, in heating the guidewire port joint 26, the guidewire port joint 26 may be heated to a temperature greater than the melting temperatures of each of the outer tubular member 70 and the inner tubular member 72 (e.g., at least one or more layers of the inner tubular member 72).

Molten material of the tubular sleeve 60 may meld with molten material of the outer tubular member 70 and molten material of the inner tubular member 72 at the guidewire port joint 26, thermally bonding the tubular sleeve 60 to the outer and inner tubular members 70, 72 to secure the midshaft section 20 with the distal section 22 of the elongate shaft 14 without using adhesive.

Figure 9B:
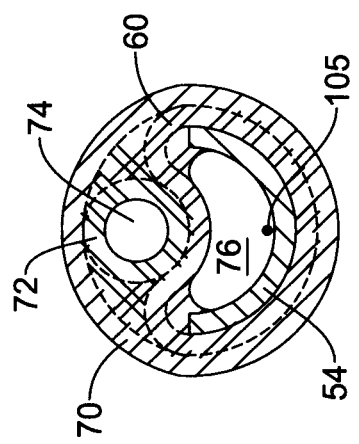
FIG. 9B is a transverse cross-sectional view of the catheter shaft taken along line 9B-9B of FIG. 9.

Additionally, as shown in FIG. 9B, molten material of the tubular sleeve 60 may surround the crescent-shaped portion of the mandrel 94 and the trough 54 of the distal skived portion 36, while melding with the molten material of the inner tubular member 72 and outer tubular member 70, encapsulating the trough 54 of the skived tubular member in the thermoplastic material of the tubular sleeve 60, such that thermoplastic material of the tubular sleeve 60 resides on each of the convex surface and the concave surface of the trough 54 to help secure the skived tubular member 30 proximate the guidewire port joint 26. Thus, the skived tubular member 30 may be secured to the outer tubular member 70 and the inner tubular member 72 without melting the skived tubular member 30 and/or using an adhesive.

Additionally, subsequent to heating the guidewire port joint 26, the mandrels 92, 94 may be removed from the lumens 74, 76.

In a further manufacturing step, a core wire 105, such as a metallic core wire may be secured to the distal portion of the proximal tubular member 80, such as by welding or adhesively bonding the core wire 105 to the proximal tubular member 80. The core wire 105 may extend distally through the lumen 46 of the skived tubular member 30 to and/or across the guidewire port joint 26. In some instances, the core wire 105 may extend distal of the distal end of the skived tubular member 30 into the inflation lumen 76 defined between the inner tubular member 72 and the outer tubular member 70 of the distal section 22.

Turning now to the proximal joint 24 shown in FIG. 8, the proximal tubular member 80 may be joined to the skived tubular member 30 such that a proximal portion of the tubular sleeve 60 extends over the junction between the proximal tubular member 80 and the skived tubular member 30. The proximal joint 24 may be formed in a similar manner as that discussed above regarding FIGS. 6 and 7.

As shown in FIG. 8, a proximal portion of the skived tubular member 30 may overlap a distal portion of the proximal tubular member 80, forming a lap joint between the skived tubular member 30 and the proximal tubular member 80. The proximal portion of the tubular sleeve 60 may extend proximally over the lap joint such that a portion of the tubular sleeve 60 is located around the proximal tubular member 80 and a portion of the tubular sleeve 60 is located around the skived tubular member 30.

The proximal joint 24 may be heated to an elevated temperature, such as greater than the melting temperature of the tubular sleeve 60. Heating of the proximal joint 24 may be performed concurrently with or separate from heating the guidewire port joint 26. In embodiments in which the proximal tubular member 80 is a metallic tubular member (e.g., hypotube) and the skived tubular member 30 is a thermoset polymer member (e.g., thermoset polyimide), the proximal joint 24 may be heated to a temperature greater than the melting temperature of the tubular sleeve 60, but below a melting temperature of the proximal tubular member 80 and below a melting temperature of the skived tubular member 30. When the tubular sleeve 60 is heated above its melting temperature, the molten material of the tubular sleeve 60 may flow around the outer surface of the proximal tubular member 80 and the skived tubular member 30.

Tapering the proximal end surface 50 of the skived tubular member 30 creates a greater surface area for the thermoplastic material of the tubular sleeve 60 to contact the interface between the proximal tubular member 80 and the skived tubular member 30. Furthermore, by tapering the proximal end surface 50 of the skived tubular member 30, polymeric material of the tubular sleeve 60 may also flow into the gap 98 between the inner surface of the skived tubular member 30 and the outer surface of the proximal tubular member 80. Radial forces exerted on the molten polymer of the tubular sleeve 60 by the heat shrink tubing may help force molten material of the tubular sleeve 60 into the gap 98.

Figure 9A:
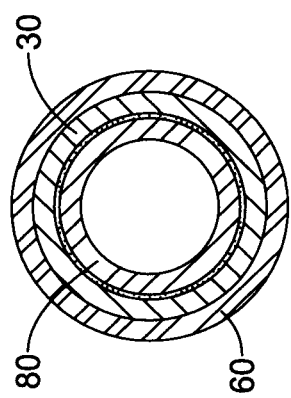
FIG. 9A is a transverse cross-sectional view of the catheter shaft taken along line 9A-9A of FIG. 9.

When heat is removed and the proximal joint 24 is allowed to cool, polymeric material of the tubular sleeve 60, as shown in FIGS. 9 and 9A, can be seen surrounding a portion of the proximal tubular member 80 and the skived tubular member 30, as well as located in the gap 98 between the inner surface of the skived tubular member 30 and the outer surface of the proximal tubular member 80. The polymeric material of the tubular sleeve 60 located in the gap 98 between the proximal tubular member 80 and the skived tubular member 30 provides a component of shear stress as well as tensile stress necessary to be overcome in order to separate the proximal tubular member 80 and the skived tubular member 30, resulting in a stronger joint.

Figure 10:
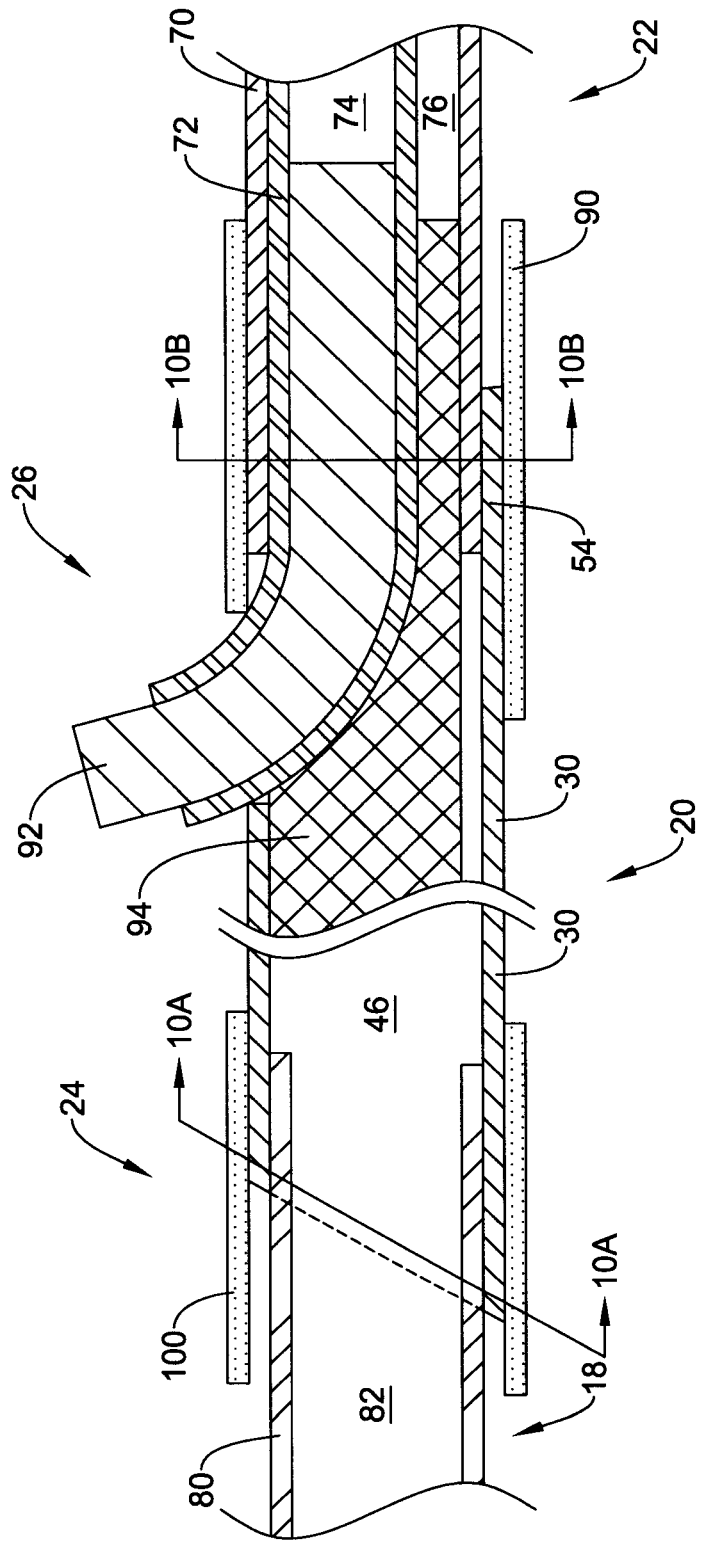
FIG. 10 is a longitudinal cross-sectional view of a fourth embodiment of a proximal joint region and a guidewire port joint region of the catheter shaft of FIG. 1 prior to heating the joint regions.
Figure 11:
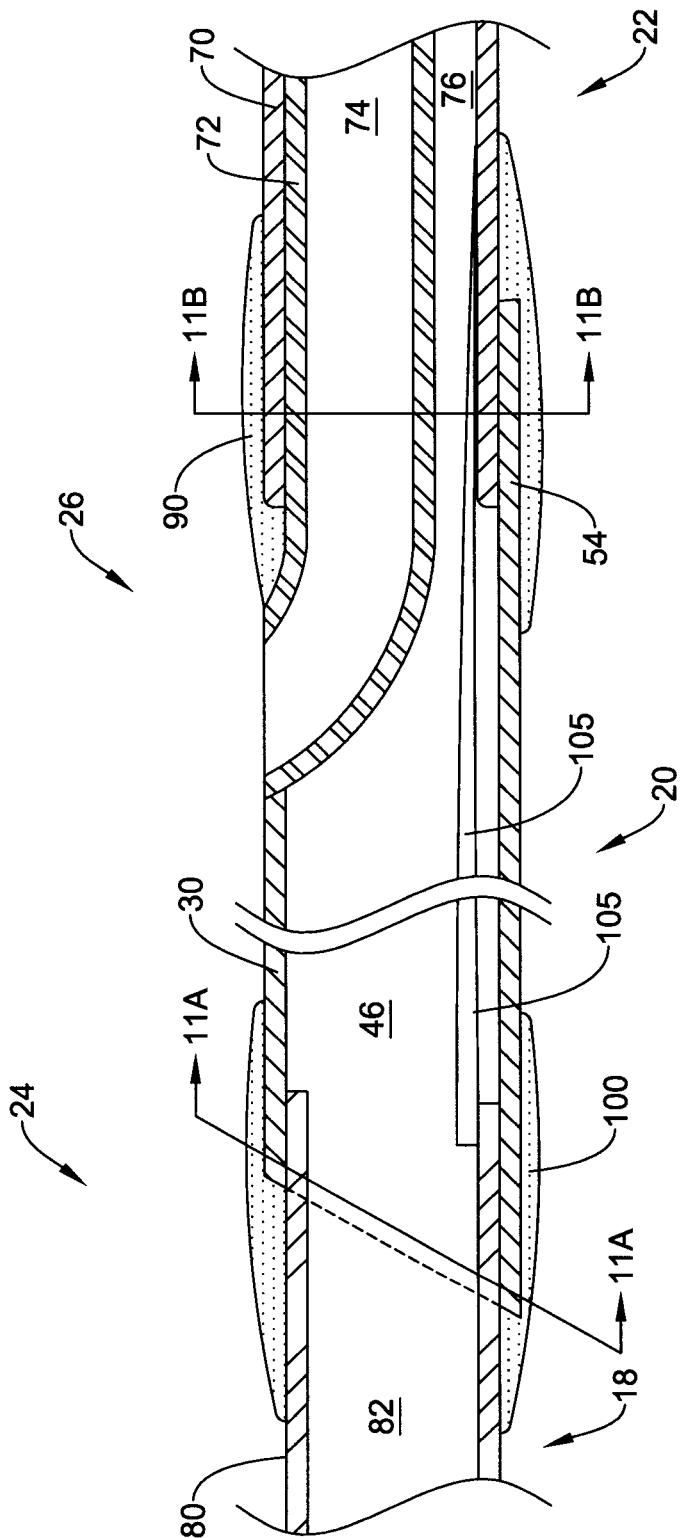
FIG. 11 is a longitudinal cross-sectional view of the joint regions of the catheter shaft shown in FIG. 10 subsequent to heating the joint regions.

FIGS. 10 and 11 illustrate a fourth embodiment of the elongate shaft 14 utilizing the skived tubular member 30, prior to heating portions of the elongate shaft 14 (FIG. 10) and subsequent to heating portions of the elongate shaft 14 (FIG. 11).

Similar to the embodiment shown in FIGS. 4 and 5, the proximal section 18 of the elongate shaft 14 may include a proximal tubular member 80 as described above. Furthermore, the distal section 22 of the elongate shaft 14 may include an outer tubular member 70 and an inner tubular member 72 extending through the outer tubular member 70 as described above.

As shown in FIG. 10, the midshaft section 20 may include the skived tubular member 30 extending distally from the proximal joint 24 to the guidewire port joint 26. The skived tubular member 30 may be secured to the proximal section 18 proximate the proximal joint 24 and may be secured to the distal section 22 proximate the guidewire port joint 26. A proximal portion of the skived tubular member 30 may be secured to the proximal tubular member 80 and a distal portion of the skived tubular member 30 may be secured to the outer tubular member 70 and/or the inner tubular member 72.

The lumen 46 of the skived tubular member 30 may be in fluid communication with each of the lumen 82 of the proximal tubular member 80 and the inflation lumen 76 defined between the inner tubular member 72 and the outer tubular member 70 of the distal section 22.

As shown in FIG. 10, in assembling the elongate shaft 14, the skived tubular member 30 may be joined to the outer and inner tubular members 70, 72 at the guidewire port joint 26. For instance, at least a portion of the distal skived portion 36 may be overlapped with a proximal portion of the outer tubular member 70 of the distal section 22. For example, at least a portion of the distal skived portion 36 of the skived tubular member 30 may be located exterior of the outer tubular member 70 such that the convex outer surface of the outer tubular member 70 faces, contacts or rests against the concave surface of the trough 54 of the distal skived portion 36. The inner tubular member 72 may extend proximally out of the outer tubular member 70 and generally follow the profile of the distal skived portion 36.

A tubular sleeve 90 may be placed around a proximal portion of the outer tubular member 70 and a distal portion of the skived tubular member 30 to bridge the interface between the skived tubular member 30 and the outer tubular member 70 at the guidewire point joint 26.

The tubular sleeve 90 may be desirably formed of a thin, thermoplastic polymeric material, similar to the tubular sleeve 60 discussed above. Some example materials may include, but are not limited to, polyamide, polyether block amide, polyurethane, silicone rubber, nylon, polyethylene, fluorinated hydrocarbon polymers, and the like. For example, in some particular examples the sleeve 60 is 100% polyamide 6, polyamide 12, or thermoplastic polyurethane. Some polymer materials suitable for use in the tubular sleeve 90 are sold under the trademarks of PEBAX, PELLETHANE, TEXIN and VESTAMID.

Also shown in FIG. 10, during the manufacturing process, a mandrel 92 may be inserted into the inner tubular member 72 to maintain the shape of the guidewire lumen 74 throughout the manufacturing process. Furthermore, a mandrel 94 (also shown in FIG. 10), which may include a crescent-shaped portion, may be inserted into the lumen 46 of the skived tubular member 30 and into the inflation lumen 76 defined between the inner tubular member 72 and the outer tubular member 70 of the distal section 22 to maintain the shape of the inflation lumen 76.

Figure 10B:
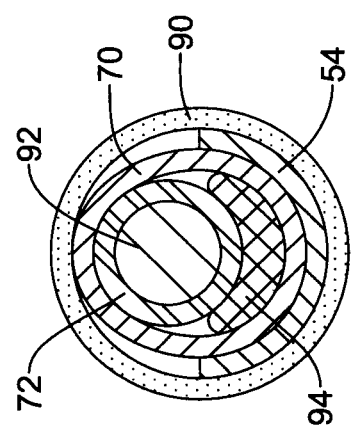
FIG. 10B is a transverse cross-sectional view of the catheter shaft taken along line 10B-10B of FIG. 10.
Figure 10A:
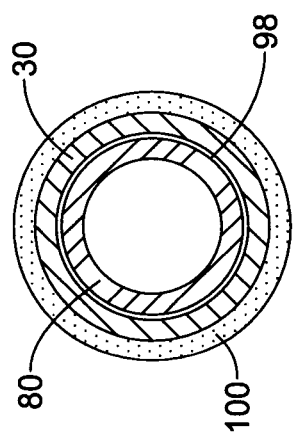
FIG. 10A is a transverse cross-sectional view of the catheter shaft taken along line 10A-10A of FIG. 10.

FIG. 10B illustrates a transverse cross-sectional view taken along line 10B-10B of FIG. 10, illustrating the arrangement of components prior to heating the guidewire port joint 26 during a manufacturing step. As can be seen from FIG. 10B, the outer tubular member 70 may be positioned in the trough 54 of the distal skived portion 36 of the skived tubular member 30 such that the concave surface of the trough 54 faces the outer surface of the outer tubular member 70 and the crescent-shaped portion of the mandrel 94 rests against the inner surface of the outer tubular member 70, between the inner tubular member 72 and the outer tubular member 70. The trough 54 is located between the sleeve 90 and the outer tubular member 70.

During a subsequent step in manufacturing the elongate shaft 14, the guidewire port joint 26 may be heated to an elevated temperature, such as greater than the melting temperature of the tubular sleeve 90. The guidewire port joint 26 may be heated by any desired heating means, for instance, laser, hot jaw or hot air, to thermally bond the thermoplastic components proximate the guidewire port joint 26. It is noted that although not shown in the drawings, during heating of the guidewire port joint 26, a length of heat shrink tubing, such as a length of polyolefin heat shrink tubing, may be placed around the sleeve 90 and adjacent portions of the elongate shaft 14 to aid in the heating process. Subsequent to heating the guidewire port joint 26, the heat shrink tubing may be removed.

In embodiments in which the skived tubular member 30 is a thermoset polymer member (e.g., thermoset polyimide), the guidewire port joint 26 may be heated to a temperature greater than the melting temperature of the tubular sleeve 90, but below a melting temperature of the skived tubular member 30. Furthermore, in heating the guidewire port joint 26, the guidewire port joint 26 may be heated to a temperature greater than the melting temperatures of each of the outer tubular member 70 and the inner tubular member 72 (e.g., at least one or more layers of the inner tubular member 72).

Figure 11B:
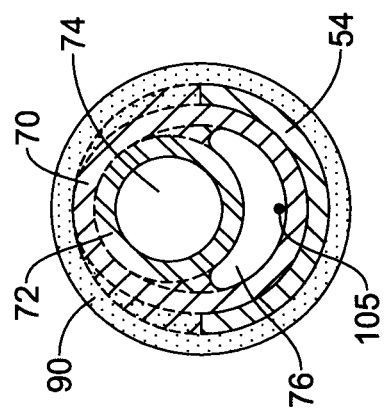
FIG. 11B is a transverse cross-sectional view of the catheter shaft taken along line 11B-11B of FIG. 11.

Molten material of the tubular sleeve 90 may surround the skived tubular member 30, the outer tubular member 70 and the portion of the inner tubular member 72 extending from the outer tubular member 70 along the distal skived portion 36 of the skived tubular member 30. When heat is removed and the guidewire port joint 26 is allowed to cool, polymeric material of the tubular sleeve 90, as shown in FIGS. 11 and 11B, can be seen surrounding a portion of the skived tubular member 30 as well as a portion of the outer tubular member 70 and the portion of the inner tubular member 72 extending out from the outer tubular member 70, sealing the guidewire port joint 26.

Furthermore, molten material of the outer tubular member 70 and/or sleeve 90 may flow around a portion of the trough 54 of the distal skived portion 36 of the skived tubular member 30 such that polymeric material of the outer tubular member 70 and/or the sleeve 90 contacts the concave surface of the trough 54 as well as the convex surface of the trough 54, encapsulating the trough 54 of the skived tubular member 30 in the thermoplastic material of the outer tubular member 70 and/or the sleeve 90. Encapsulation of the trough 54 such that thermoplastic material of the outer tubular member 70 and/or the sleeve 90 resides on each of the convex surface and the concave surface of the trough 54 may help secure the skived tubular member 30 to the distal section 22 of the elongate shaft 14, preventing deflection of the trough 54 during catheter bending. Thus, the skived tubular member 30 may be secured to the distal section 22 without melting the skived tubular member 30 and/or using an adhesive.

Additionally, subsequent to heating the guidewire port joint 26, the mandrels 92, 94 may be removed from the lumens 74, 76, and the excess portion of the inner tubular member 72 which extends outward from the outer surface of the skived tubular member 30 may be trimmed away as shown in FIG. 11.

In a further manufacturing step, a core wire 105, such as a metallic core wire may be secured to the distal portion of the proximal tubular member 80, such as by welding or adhesively bonding the core wire 105 to the proximal tubular member 80. The core wire 105 may extend distally through the lumen 46 of the skived tubular member 30 to and/or across the guidewire port joint 26. In some instances, the core wire 105 may extend distal of the distal end of the skived tubular member 30 into the inflation lumen 76 defined between the inner tubular member 72 and the outer tubular member 70 of the distal section 22.

Turning now to the proximal joint 24 shown in FIG. 10, the proximal tubular member 80 may be joined to the skived tubular member 30 using a tubular sleeve 100 in a similar manner as that discussed above regarding FIGS. 4 and 5. The tubular sleeve 100 may be desirably formed of a thin, thermoplastic polymeric material, similar to the tubular sleeve 60 discussed above.

As shown in FIG. 10, a proximal portion of the skived tubular member 30 may be overlapped with a distal portion of the proximal tubular member 80, forming a lap joint between the skived tubular member 30 and the proximal tubular member 80. The tubular sleeve 100 may be positioned over the lap joint such that a portion of the tubular sleeve 100 is located around the proximal tubular member 80 and a portion of the tubular sleeve 100 is located around the skived tubular member 30.

During a subsequent step in manufacturing the elongate shaft 14, the proximal joint 24 may be heated to an elevated temperature, such as greater than the melting temperature of the tubular sleeve 100. Heating of the proximal joint 24 may be performed concurrently with or separate from heating the guidewire port joint 26. The proximal joint 24 may be heated by any desired heating means, for instance, laser, hot jaw or hot air. It is noted that although not shown in the drawings, during heating of the proximal joint 24, a length of heat shrink tubing, such as a length of polyolefin heat shrink tubing, may be placed around the sleeve 100 and adjacent portions of the elongate shaft 14 to aid in the heating process. Subsequent to heating the proximal joint 24, the heat shrink tubing may be removed.

In embodiments in which the proximal tubular member 80 is a metallic tubular member (e.g., hypotube) and the skived tubular member 30 is a thermoset polymer member (e.g., thermoset polyimide), the proximal joint 24 may be heated to a temperature greater than the melting temperature of the tubular sleeve 100, but below a melting temperature of the proximal tubular member 80 and below a melting temperature of the skived tubular member 30. When the tubular sleeve 100 is heated above its melting temperature, the molten material of the tubular sleeve 100 may flow around the outer surface of the proximal tubular member 80 and the skived tubular member 30.

Figure 11A:
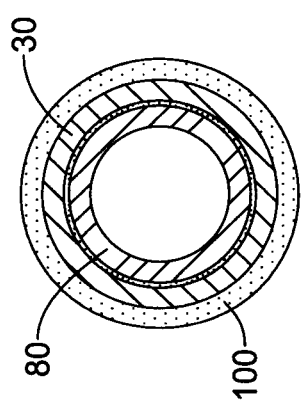
FIG. 11A is a transverse cross-sectional view of the catheter shaft taken along line 11A-11A of FIG. 11.

Tapering the proximal end surface 50 of the skived tubular member 30 creates a greater surface area for the thermoplastic material of the tubular sleeve 100 to contact the interface between the proximal tubular member 80 and the skived tubular member 30. Furthermore, by tapering the proximal end surface 50 of the skived tubular member 30, polymeric material of the tubular sleeve 100 may also flow into the gap 98 between the inner surface of the skived tubular member 30 and the outer surface of the proximal tubular member 80. Radial forces exerted on the molten polymer of the tubular sleeve 100 by the heat shrink tubing may help force molten material of the tubular sleeve 100 into the gap 98. When heat is removed and the proximal joint 24 is allowed to cool, polymeric material of the tubular sleeve 100, as shown in FIGS. 11 and 11A, can be seen surrounding a portion of the proximal tubular member 80 and the skived tubular member 30, as well as located in the gap 98 between the inner surface of the skived tubular member 30 and the outer surface of the proximal tubular member 80. The polymeric material of the tubular sleeve 100 located in the gap 98 between the proximal tubular member 80 and the skived tubular member 30 provides a component of shear stress as well as tensile stress necessary to be overcome in order to separate the proximal tubular member 80 and the skived tubular member 30, resulting in a stronger joint.

The skived tubular member 30 formed of a thermoset polymer material, included in the catheter construction of the various embodiments disclosed herein, provides enhanced rigidity to the midshaft section 20 of the elongate shaft 14, which improves the pushability of the elongate shaft 14 over midshaft sections using thermoplastic polymer materials. By encapsulating at least a portion of the trough 54 of the skived tubular with thermoplastic material from one or more additional components of the elongate shaft 14 during a heating process, the trough 54 may be mechanically locked in the elongate shaft 14 without the need of adhesives, providing strong, reliable securement of the skived tubular member 30 with the distal shaft section 22 proximate the guidewire port joint 26. Additionally, the portions of the elongate shaft 14 formed of thermoplastic materials may be thermally bonded together during the heating process of the proximal joint 24 and/or the guidewire port joint 26.

Furthermore, the trough 54 of the skived tubular member 30, because it does not melt during the heating process, helps insure against inadvertent thinning of the catheter wall at the guidewire port joint 26 which may weaken the catheter wall. Such weakening of the catheter wall has been found to lead to failure of the catheter 10, such as leaking or rupture of the inflation lumen 76.

Additionally, as with the embodiment shown in FIGS. 8 and 9, the septum (i.e., the catheter material located directly between the guidewire lumen 74 and the inflation lumen 76) of the distal section 22, may have an increased thickness due to being formed of material from both the crescent-shaped portion 64 of the sleeve 60 and the inner tubular member 72.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A medical catheter comprising:
a hub assembly; and
an elongate shaft extending distally from the hub assembly, the elongate shaft including a proximal section, a midshaft section extending distally from the proximal section with a proximal portion of the midshaft section overlapping a distal portion of the proximal section to form a proximal joint, and a distal section extending distally from the midshaft section and at least partially overlapping the midshaft section to form a distal joint;
wherein the proximal section includes a first tubular member;
wherein the midshaft section includes a second tubular member and a thermoplastic tubular sleeve extending over the second tubular member, a proximal portion of the second tubular member joined to a distal portion of the first tubular member at the proximal joint;
wherein the distal section includes an outer tubular member and an inner tubular member disposed within the outer tubular member, the inner and outer tubular members extending distally from the distal joint, wherein the inner tubular member defines a guidewire lumen extending distally from a guidewire port located at the distal joint, the guidewire port providing access to the guidewire lumen from exterior of the elongate shaft; and wherein the thermoplastic tubular sleeve is bonded to at least one of the inner tubular member and the outer tubular member of the distal section at the distal joint and extends proximally to the proximal joint to a location proximal of a proximal end of the second tubular member such that a proximal portion of the thermoplastic tubular sleeve surrounds a portion of the first tubular member.

2. The medical catheter of claim 1, wherein the thermoplastic tubular sleeve includes a crescent-shaped tubular portion defining a crescent-shaped lumen, wherein a distal end portion of the second tubular member is located within the crescent-shaped lumen of the crescent-shaped tubular portion of the thermoplastic tubular sleeve.

3. The medical catheter of claim 1, wherein the thermoplastic tubular sleeve is bonded to both the inner tubular member and the outer tubular member of the distal section at the distal joint.

4. The medical catheter of claim 1, wherein a distal end of the thermoplastic tubular sleeve extends into a proximal portion of the outer tubular member of the distal section.

5. The medical catheter of claim 1, wherein a distal portion of the first tubular member extends into a proximal portion of the second tubular member, forming a lap joint.

6. The medical catheter of claim 5, wherein the second tubular member has a longitudinal axis, and wherein the second tubular member has a proximal end surface at an oblique angle to the longitudinal axis.

7. The medical catheter of claim 6, wherein material of the thermoplastic tubular sleeve is located in a gap between an inner surface of the second tubular member and an outer surface of the first tubular member at the proximal joint.

8. The medical catheter of claim 1, wherein the first tubular member is a metallic hypotube.

9. The medical catheter of claim 8, wherein the thermoplastic tubular sleeve is heat shrunk around the metallic hypotube at the proximal joint to secure the metallic hypotube to the second tubular member.

10. The medical catheter of claim 9, wherein material of the thermoplastic tubular sleeve is located in a gap between an inner surface of the second tubular member and an outer surface of the metallic hypotube at the proximal joint.

11. A medical catheter comprising:

a hub assembly; and an elongate shaft extending distally from the hub assembly, the elongate shaft including a proximal section, a midshaft section extending distally from the proximal section with a proximal portion of the midshaft section overlapping a distal portion of the proximal section to form a proximal joint, and a distal section extending distally from the midshaft section and at least partially overlapping the midshaft section to form a distal joint;

wherein the proximal section includes a first tubular member;

wherein the midshaft section includes a second tubular member having a longitudinal axis and a proximal end surface at an oblique angle to the longitudinal axis, a proximal portion of the second tubular member surrounding a distal portion of the first tubular member at the proximal joint;

wherein the distal section includes an outer tubular member and an inner tubular member disposed within the outer tubular member, the inner and outer tubular members extending distally from the distal joint, wherein the inner tubular member defines a guidewire lumen extending distally from a guidewire port located at the distal joint, the guidewire port providing access to the guidewire lumen from exterior of the elongate shaft; and wherein the proximal joint includes a thermoplastic tubular sleeve overlapping the proximal joint such that a first portion of the thermoplastic tubular sleeve surrounds and contacts an outer surface of the first tubular member, and a second portion of the thermoplastic tubular sleeve surrounds and contacts an outer surface of the second tubular member.

12. The medical catheter of claim 11, wherein the thermoplastic tubular sleeve extends distally to the distal joint and is bonded to at least one of the inner tubular member and the outer tubular member of the distal section at the distal joint.

13. The medical catheter of claim 11, wherein the thermoplastic tubular sleeve extends distally to the distal joint and is bonded to both the inner tubular member and the outer tubular member of the distal section at the distal joint.

14. The medical catheter of claim 13, wherein the thermoplastic tubular sleeve includes a crescent-shaped tubular portion defining a crescent-shaped lumen, wherein a distal end portion of the second tubular member is located within the crescent-shaped lumen of the crescent-shaped tubular portion of the thermoplastic tubular sleeve.

15. The medical catheter of claim 11, wherein a distal end of the thermoplastic tubular sleeve extends into a proximal portion of the outer tubular member of the distal section.

16. The medical catheter of claim 11, wherein material of the thermoplastic tubular sleeve is located in a gap between an inner surface of the second tubular member and an outer surface of the first tubular member at the proximal joint.

17. The medical catheter of claim 11, wherein the first tubular member is a metallic hypotube.

18. The medical catheter of claim 17, wherein the thermoplastic tubular sleeve is heat shrunk around the metallic hypotube at the proximal joint to secure the metallic hypotube to the second tubular member.

19. The medical catheter of claim 18, wherein material of the thermoplastic tubular sleeve is located in a gap between an inner surface of the second tubular member and an outer surface of the metallic hypotube at the proximal joint.

* * * * *